United States Patent
Koo et al.

(10) Patent No.: US 12,126,683 B2
(45) Date of Patent: Oct. 22, 2024

(54) PRIVACY SWITCH FOR MOBILE COMMUNICATIONS DEVICE

(71) Applicant: Masimo Corporation, Irvine, CA (US)

(72) Inventors: Peter Koo, Irvine, CA (US); Massi Joe E. Kiani, Laguna Niguel, CA (US); Bilal Muhsin, Irvine, CA (US); Omar Ahmed, Lake Forest, CA (US); Richard Priddell, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 17/823,719

(22) Filed: Aug. 31, 2022

(65) Prior Publication Data

US 2023/0069789 A1 Mar. 2, 2023

Related U.S. Application Data

(60) Provisional application No. 63/260,744, filed on Aug. 31, 2021.

(51) Int. Cl.
*H04B 1/3827* (2015.01)
*A61B 5/024* (2006.01)
(Continued)

(52) U.S. Cl.
CPC .............. *H04L 67/12* (2013.01); *H04W 4/38* (2018.02)

(58) Field of Classification Search
CPC .............. A61B 5/024; G06F 21/6245; H04B 2001/3861; H04B 1/385; H04M 1/72409; H04L 67/12; H04W 4/38
See application file for complete search history.

(56) References Cited

U.S. PATENT DOCUMENTS

| | | |
|---|---|---|
| 4,509,531 A | 4/1985 | Ward |
| 4,819,860 A | 4/1989 | Hargrove et al. |
| | (Continued) | |

FOREIGN PATENT DOCUMENTS

| | | |
|---|---|---|
| AU | 2016323049 | 4/2018 |
| CN | 103441998 | 12/2013 |
| | (Continued) | |

OTHER PUBLICATIONS

US 2022/0192529 A1, 06/2022, Al-Ali et al. (withdrawn)
(Continued)

*Primary Examiner* — Chris Parry
*Assistant Examiner* — Hassan A Khan
(74) *Attorney, Agent, or Firm* — Knobbe, Martens, Olson & Bear, LLP

(57) ABSTRACT

A mobile device may comprise: a power source, one or more sensors, a communication device, and an actuator. The power source can be configured to provide power to one or more components of the mobile device. The one or more sensors can be configured to generate sensor data. The communication device can be removably coupled to the power source to receive power therefrom and can be further configured to communicate with one or more computing devices remote to the mobile device. The actuator can be configured to transition between at least a first state and a second state to cause the communication device to electrically disconnect from the power source to terminate communication of the communication device with the one or more computing devices remote to the mobile device. The one or more sensors can be configured to generate sensor data when the actuator is in the first state or the second state.

21 Claims, 18 Drawing Sheets

(51) Int. Cl.
  *G06F 21/62* (2013.01)
  *H04L 67/12* (2022.01)
  *H04W 4/38* (2018.01)

(56) References Cited

U.S. PATENT DOCUMENTS

| | | | |
|---|---|---|---|
| 4,960,128 A | 10/1990 | Gordon et al. |
| 4,964,408 A | 10/1990 | Hink et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,434,562 A | 7/1995 | Reardon |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,272,533 B1 | 8/2001 | Browne |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,605,038 B1 | 8/2003 | Teller et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,801,799 B2 | 10/2004 | Mendelson |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |

(56) References Cited

U.S. PATENT DOCUMENTS

| | | |
|---|---|---|
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| D608,225 S | 1/2010 | Giroud |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| D626,147 S | 10/2010 | Goddard |
| RE41,912 E | 11/2010 | Parker |
| D628,110 S | 11/2010 | Boulangeot |
| D630,961 S | 1/2011 | Ciuchindel et al. |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| 8,090,961 B2 | 1/2012 | Yoffe et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Ai-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| D685,367 S | 7/2013 | Akana et al. |
| 8,509,867 B2 | 8/2013 | Workman et al. |
| 8,515,509 B2 | 8/2013 | Bruinsma et al. |
| 8,522,309 B2 | 8/2013 | Yoffe et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| D694,745 S | 12/2013 | Akana et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Ai-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| D709,873 S | 7/2014 | Aumiller et al. |
| D709,874 S | 7/2014 | Aumiller et al. |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| D711,372 S | 8/2014 | Aumiller et al. |
| D711,873 S | 8/2014 | Aumiller et al. |
| 8,801,613 B2 | 8/2014 | Al-Ali et al. |
| D712,930 S | 9/2014 | Lee et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,896,754 B2 | 11/2014 | Mundt et al. |
| 8,897,847 B2 | 11/2014 | Al-Ali |
| 8,911,377 B2 | 12/2014 | Al-Ali |
| 8,924,708 B2 | 12/2014 | Yoffe et al. |
| D724,103 S | 3/2015 | Akana et al. |
| 8,989,831 B2 | 3/2015 | Al-Ali et al. |
| D727,316 S | 4/2015 | Song |
| 8,998,809 B2 | 4/2015 | Kiani |
| D729,238 S | 5/2015 | Song |
| D729,796 S | 5/2015 | Song |
| D730,347 S | 5/2015 | Jung et al. |
| D732,527 S | 6/2015 | Kim et al. |
| D732,528 S | 6/2015 | Kim et al. |
| D733,132 S | 6/2015 | Kim et al. |
| D733,133 S | 6/2015 | Kim et al. |
| 9,066,666 B2 | 6/2015 | Kiani |
| 9,066,680 B1 | 6/2015 | Al-Ali et al. |
| D735,190 S | 7/2015 | Song |
| 9,092,642 B2 | 7/2015 | Prakash et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,513 S | 12/2015 | Jung et al. |
| D745,514 S | 12/2015 | Jung et al. |
| 9,211,095 B1 | 12/2015 | Al-Ali |
| 9,218,454 B2 | 12/2015 | Kiani et al. |
| D746,868 S | 1/2016 | Akana et al. |
| 9,245,668 B1 | 1/2016 | Vo et al. |
| 9,267,572 B2 | 2/2016 | Barker et al. |

(56) References Cited

U.S. PATENT DOCUMENTS

| | | |
|---|---|---|
| D751,069 S | 3/2016 | Choi et al. |
| D752,580 S | 3/2016 | Choi et al. |
| D752,582 S | 3/2016 | Jung et al. |
| 9,277,880 B2 | 3/2016 | Poeze et al. |
| D753,510 S | 4/2016 | Puttorngul et al. |
| 9,307,928 B1 | 4/2016 | Al-Ali et al. |
| 9,323,894 B2 | 4/2016 | Kiani |
| D755,176 S | 5/2016 | Jung et al. |
| D755,392 S | 5/2016 | Hwang et al. |
| D757,819 S | 5/2016 | Akana et al. |
| 9,326,712 B1 | 5/2016 | Kiani |
| D759,120 S | 6/2016 | Akana et al. |
| D760,220 S | 6/2016 | Aumiller et al. |
| 9,392,945 B2 | 7/2016 | Al-Ali et al. |
| 9,408,542 B1 | 8/2016 | Kinast et al. |
| D766,115 S | 9/2016 | Ma |
| D766,235 S | 9/2016 | Song |
| 9,436,645 B2 | 9/2016 | Al-Ali et al. |
| 9,445,759 B1 | 9/2016 | Lamego et al. |
| D768,622 S | 10/2016 | Kim et al. |
| D768,724 S | 10/2016 | Akana et al. |
| 9,474,474 B2 | 10/2016 | Lamego et al. |
| D770,533 S | 11/2016 | Akana et al. |
| D771,624 S | 11/2016 | Aumiller et al. |
| D772,228 S | 11/2016 | Jung et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| D780,223 S | 2/2017 | Kim |
| 9,560,996 B2 | 2/2017 | Kiani |
| 9,579,039 B2 | 2/2017 | Jansen et al. |
| D782,537 S | 3/2017 | Akana et al. |
| 9,622,692 B2 | 4/2017 | Lamego et al. |
| D787,714 S | 5/2017 | Wang et al. |
| D788,079 S | 5/2017 | Son et al. |
| D788,312 S | 5/2017 | Al-Ali et al. |
| 9,649,054 B2 | 5/2017 | Lamego et al. |
| 9,664,556 B2 * | 5/2017 | Chu .................. H01L 31/0232 |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| D797,809 S | 9/2017 | Akana et al. |
| D797,810 S | 9/2017 | Akana et al. |
| 9,750,415 B2 | 9/2017 | Breslow et al. |
| 9,750,442 B2 | 9/2017 | Olsen |
| 9,750,461 B1 | 9/2017 | Telfort |
| D800,172 S | 10/2017 | Akana et al. |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| D806,063 S | 12/2017 | Kim |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| D807,351 S | 1/2018 | Bang et al. |
| 9,861,298 B2 | 1/2018 | Eckerbom et al. |
| 9,861,305 B1 | 1/2018 | Weber et al. |
| 9,871,974 B2 | 1/2018 | Robinson et al. |
| 9,877,650 B2 | 1/2018 | Muhsin et al. |
| D809,512 S | 2/2018 | Mistry et al. |
| 9,891,079 B2 | 2/2018 | Dalvi |
| D812,607 S | 3/2018 | Mistry et al. |
| 9,924,897 B1 | 3/2018 | Abdul-Hafiz |
| 9,936,917 B2 | 4/2018 | Poeze et al. |
| D816,524 S | 5/2018 | Akana et al. |
| D819,021 S | 5/2018 | Mistry et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| D823,301 S | 7/2018 | Bang et al. |
| 10,010,276 B2 | 7/2018 | Al-Ali et al. |
| D827,831 S | 9/2018 | Fong et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| D839,753 S | 2/2019 | Domke et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| 10,243,824 B2 | 3/2019 | Zalmanovitch et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D861,676 S | 10/2019 | Mistry et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| D866,350 S | 11/2019 | Park et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| D875,092 S | 2/2020 | Akana et al. |
| 10,555,678 B2 | 2/2020 | Dalvi et al. |
| 10,568,553 B2 | 2/2020 | O'Neil et al. |
| 10,608,817 B2 | 3/2020 | Haider et al. |
| D880,477 S | 4/2020 | Forrest et al. |
| D882,565 S | 4/2020 | Akana et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| 10,860,735 B2 | 12/2020 | Naqvi et al. |
| D906,970 S | 1/2021 | Forrest et al. |

(56) References Cited

U.S. PATENT DOCUMENTS

| | | |
|---|---|---|
| D908,213 S | 1/2021 | Abdul-Hafiz et al. |
| 10,918,281 B2 | 2/2021 | Al-Ali et al. |
| 10,930,452 B2 | 2/2021 | Weaver |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Ai-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| D949,144 S | 4/2022 | Akana et al. |
| D949,145 S | 4/2022 | Akana et al. |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D953,324 S | 5/2022 | Akana et al. |
| D957,648 S | 7/2022 | Ai-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| D962,933 S | 9/2022 | Akana et al. |
| D962,934 S | 9/2022 | Akana et al. |
| D962,936 S | 9/2022 | Akana et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,490,248 B2 | 11/2022 | Baker et al. |
| 11,504,057 B2 * | 11/2022 | Clavelle ............... A61B 5/681 |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| 11,559,275 B2 * | 1/2023 | Telfort .................... A61B 7/00 |
| D979,516 S | 2/2023 | Al-Ali et al. |
| 11,574,781 B2 | 2/2023 | Weaver |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| 11,951,186 B2 | 4/2024 | Krishnamani et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2004/0195460 A1 | 10/2004 | Sailer |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0208925 A1 | 8/2008 | Shum |
| 2008/0215841 A1 | 9/2008 | Bolotin et al. |
| 2008/0221418 A1 | 9/2008 | Al-Ali et al. |
| 2009/0036759 A1 | 2/2009 | Ault et al. |
| 2009/0054751 A1 | 2/2009 | Babashan et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0271121 A1 * | 10/2012 | Della Torre ............ A61B 5/01 600/479 |
| 2012/0283524 A1 | 11/2012 | Kiani et al. |
| 2013/0023775 A1 | 1/2013 | Lamego et al. |
| 2013/0060147 A1 | 3/2013 | Welch et al. |

(56) References Cited

U.S. PATENT DOCUMENTS

| | | |
|---|---|---|
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0278229 A1 | 9/2014 | Hong et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0250396 A1* | 9/2015 | Ahmed .............. A61B 5/02427 600/508 |
| 2015/0288882 A1 | 10/2015 | Haddad et al. |
| 2016/0063893 A1* | 3/2016 | Kanuganti ......... H04N 21/8545 348/62 |
| 2016/0196388 A1 | 7/2016 | Lamego |
| 2016/0206221 A1* | 7/2016 | Kim ........................ A61B 5/681 |
| 2016/0206251 A1* | 7/2016 | Kwon ................. A61B 5/02427 |
| 2016/0240721 A1* | 8/2016 | Chu ...................... G01J 1/0214 |
| 2016/0324432 A1 | 11/2016 | Ahmed et al. |
| 2016/0334332 A1 | 11/2016 | Magnussen et al. |
| 2016/0367173 A1 | 12/2016 | Dalvi et al. |
| 2017/0024748 A1 | 1/2017 | Haider |
| 2017/0086743 A1 | 3/2017 | Bushnell et al. |
| 2017/0173632 A1 | 6/2017 | Al-Ali |
| 2017/0215743 A1 | 8/2017 | Meer et al. |
| 2017/0251974 A1 | 9/2017 | Shreim et al. |
| 2017/0263254 A1 | 9/2017 | Dewan et al. |
| 2017/0290552 A1* | 10/2017 | Naruse ..................... A61B 5/681 |
| 2017/0325744 A1 | 11/2017 | Allec et al. |
| 2018/0167806 A1* | 6/2018 | Boyd ................ H04M 1/72454 |
| 2018/0235542 A1 | 8/2018 | Yun et al. |
| 2018/0242926 A1 | 8/2018 | Muhsin et al. |
| 2018/0247712 A1 | 8/2018 | Muhsin et al. |
| 2018/0360326 A1 | 12/2018 | Lee et al. |
| 2019/0082968 A1* | 3/2019 | Karnik ...................... A61B 5/01 |
| 2019/0090806 A1* | 3/2019 | Clavelle ................ A61B 5/681 |
| 2019/0196411 A1 | 6/2019 | Yuen |
| 2019/0239787 A1 | 8/2019 | Pauley et al. |
| 2019/0320906 A1 | 10/2019 | Olsen |
| 2019/0324593 A1 | 10/2019 | Chung et al. |
| 2019/0374713 A1 | 12/2019 | Kiani et al. |
| 2020/0020493 A1 | 1/2020 | Weaver |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113496 A1 | 4/2020 | Scruggs et al. |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0196141 A1 | 6/2020 | Baker et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Ai-Ai |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0358700 A1 | 11/2021 | Weaver |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0219311 A1* | 7/2022 | Duthaler ............... A47L 9/2857 |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Ai-Ali |
| 2023/0058342 A1 | 2/2023 | Kiani |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |

FOREIGN PATENT DOCUMENTS

| | | |
|---|---|---|
| CN | 302942795 S | 9/2014 |
| CN | 302972990 S | 10/2014 |
| CN | 303285726 S | 7/2015 |
| CN | 303296619 S | 7/2015 |
| CN | 303306604 S | 7/2015 |
| CN | 303327831 S | 8/2015 |
| CN | 303518893 S | 12/2015 |
| CN | 303646405 S | 4/2016 |
| CN | 303737075 S | 7/2016 |
| CN | 106161481 | 11/2016 |
| CN | 304027493 S | 2/2017 |
| CN | 106485113 | 3/2017 |
| CN | 106527106 | 3/2017 |
| CN | 304385323 S | 12/2017 |
| CN | 304481666 S | 1/2018 |

(56) References Cited

FOREIGN PATENT DOCUMENTS

| | | |
|---|---|---|
| EM | 001383434-0008 | 9/2013 |
| EM | 001383434-0009 | 9/2013 |
| EM | 002743575-0001 | 7/2015 |
| EM | 004428274-0003 | 10/2017 |
| EM | 005940459-0005 | 12/2018 |
| EM | 005940459-0011 | 12/2018 |
| EM | 005940459-0013 | 12/2018 |
| EM | 005940459-0014 | 12/2018 |
| EM | 005940459-0015 | 12/2018 |
| EM | 006302279-0001 | 3/2019 |
| EM | 006302279-0002 | 3/2019 |
| EM | 007127113-0001 | 10/2019 |
| EP | 3019073 | 5/2016 |
| EP | 3313276 | 5/2018 |
| EP | 3 459 447 | 3/2019 |
| JP | 2007-006363 | 1/2007 |
| JP | D1568369 | 12/2016 |
| KR | 30-0740673 | 4/2014 |
| KR | 30-0817671 | 9/2015 |
| KR | 10-2019-0115313 | 10/2019 |
| WO | WO 2008/040736 | 4/2008 |
| WO | WO 2012/092221 | 7/2012 |
| WO | WO D083678-002 | 6/2014 |
| WO | WO D086018-0001 | 3/2015 |
| WO | WO D086018-0002 | 3/2015 |
| WO | WO D086693-004 | 7/2015 |
| WO | WO 2017/165532 | 9/2017 |
| WO | WO 2018/112401 | 6/2018 |
| WO | WO 2020/006477 | 1/2020 |
| WO | WO 2021/146333 | 7/2021 |
| WO | WO 2023/287789 | 1/2023 |
| WO | WO 2023/034879 | 3/2023 |

OTHER PUBLICATIONS

US 2024/0016391 A1, 01/2024, Lapotko et al. (withdrawn)
U.S. Appl. No. 62/691,822, filed Jun. 29, 2018, Weaver.
Invitation to Pay Additional Fees from International Application No. PCT/US2021/013299, dated Apr. 29, 2021, 16 pages.
International Search Report and Written Opinion received in International Application No. PCT/US2021/013299, dated Jun. 21, 2021, 23 pages.
International Search Report and Written Opinion received in International Application No. PCT/US2022/036823, dated Oct. 21, 2022, 13 pages.
International Search Report and Written Opinion received in International Application No. PCT/US2022/075787, dated Dec. 13, 2022, 12 pages.
Jung, Scott, "Medgadget Joins the Verily Baseline Project Study, Part 2: The Tech", MedGadget.com, https://www.medgadget.com/2017/10/medgadget-joins-verily-baseline-project-study-part-2-tech.html, Oct. 27, 2017, pp. 6.
U.S. Appl. No. 60/881,510, filed Jan. 22, 2007, Yoffe et al.
Paradesi, Sharon, "User-controlled Privacy for Personal Mobile Data;" 82 pages (2014).
Sekhar et al., Health Emergency Alarm for Rigorous Treatment (HEART), International Journal of Engineering Research in Computer Science and Engineering (IJERCSE), vol. 5, Issue 4, Apr. 2018; 9 pages.
Zhu et al., "Privacy paradox in mHealth applications: An integrated elaboration likelihood model incorporating privacy calculus and privacy fatigue," Telematics and Informatics 61, 101601; 15 pages (2021).

* cited by examiner

PRIVACY SWITCH FOR MOBILE COMMUNICATIONS DEVICE

CROSS-REFERENCE TO RELATED APPLICATIONS

This application claims the benefit of U.S. Provisional Application No. 63/260,744, filed Aug. 31, 2021. The entire disclosure of each of the above items is hereby made part of this specification as if set forth fully herein and incorporated by reference for all purposes, for all that it contains.

FIELD

The present disclosure relates to privacy settings on a mobile communications device, including devices and methods for protecting sensitive or personal data on a mobile communications device. The present disclosure also relates to devices and methods for monitoring and modifying radio frequency energy emitted by a mobile communications device.

BACKGROUND

Mobile devices can collect and maintain data which can include sensitive or personal data. Mobile devices can wirelessly communicate data to remote computing devices and servers. Mobile devices and cell towers use radio frequency (RF) radiation to transmit and receive signals. Wi-Fi and other wireless technologies use RF radiation as well. RF radiation, which includes radio waves and microwaves, has raised health concerns. In particular, concerns have been raised that the RF radiation emitted by a phone call may increase a user's health risk, such as the user's risk of cancer or tumors.

SUMMARY

For purposes of summarizing the disclosure, certain aspects, advantages and novel features of the inventions have been described herein. It is to be understood that not necessarily all such advantages can be achieved in accordance with any particular aspect of the inventions disclosed herein. Thus, the inventions disclosed herein can be embodied or carried out in a manner that achieves or optimizes one advantage or group of advantages as taught herein without necessarily achieving other advantages as can be taught or suggested herein.

Disclosed herein is a healthcare-focused mobile device that includes software, firmware, hardware, or any combination thereof to provide or facilitate healthcare related services or applications. The mobile device may facilitate monitoring and/or management of one or more physiological parameters or blood analytes. The mobile device may facilitate connections with caregivers or other health-related services or individuals. The mobile device may include user-configurable hardware or software allowing for modification of health-care related applications. For example, the mobile device may include hardware or software configurations that allows a user to adjust privacy-related settings (for example, restricting sensitive and personal data) or health related settings (for example, RF energy). In some cases, the mobile device can manage the data by tagging it as sensitive data and then adjusting settings based on the tagged data A healthcare-focused mobile device with cellular capabilities that facilitates adjustments to radio frequency (RF) energy produced by the mobile device. The adjustments may occur automatically, such as in response to a condition being satisfied. In addition or alternatively, the adjustments may occur responsive to user input. As a result, the RF energy emissions can be tuned to a desired level, which can vary based on the user's risk tolerance.

Disclosed herein is a mobile device which may comprise: a power source, one or more sensors, a communication device, and an actuator. The power source can be configured to provide power to one or more components of the mobile device. The one or more sensors can be configured to generate sensor data. The communication device can be removably coupled to the power source to receive power therefrom and can be further configured to communicate with one or more computing devices remote to the mobile device. The actuator can be configured to transition between at least a first state and a second state to cause the communication device to electrically disconnect from the power source to terminate communication of the communication device with the one or more computing devices remote to the mobile device. The one or more sensors can be configured to generate sensor data when the actuator is in the first state or the second state.

In some implementations, the one or more sensors are configured to generate sensor data when the communication device is electrically disconnected from the power source.

In some implementations, the one or more sensors are electrically coupled to the power source when the actuator is in the first state or the second state.

In some implementations, the mobile device may further comprise: a computer readable storage medium having program instructions embodied therewith relating to one or more applications of the one or more sensors; and one or more processors configured to execute the program instructions to cause the mobile device to perform one or more operations of the one or more applications when the actuator is in the first state or the second state.

In some implementations, the mobile device may further comprise: a data storage device configured to store sensor data generated by the one or more sensors, wherein the data storage device is configured to receive the sensor data when the actuator is in the first state or the second state.

In some implementations, the mobile device may further comprise: a hardware processor in communication with the one or more sensors and configured to execute program instructions to cause the one or more sensors to perform one or more operations, wherein the hardware processor is configured to communicate with the one or more sensors when the actuator is in the first state or the second state.

In some implementations, the mobile device may further comprise one or more hardware processors. The one or more hardware processors may be configured to execute program instructions to cause the mobile device to access first sensor data generated by the one or more sensors when the actuator is in a first state. The one or more hardware processors may be configured to execute program instructions to cause the mobile device to store said first sensor data in a first partition of memory of a storage device of the mobile device. The one or more hardware processors may be configured to execute program instructions to cause the mobile device to access second sensor data generated by the one or more sensors when the actuator is in a second state. The one or more hardware processors may be configured to execute program instructions to cause the mobile device to store said second sensor data in the first partition of memory of the storage device.

In some implementations, the actuator is physically separate from the one or more sensors.

In some implementations, the actuator does not mechanically prevent the one or more sensors from obtaining data.

In some implementations, transitioning the actuator between the first state and the second state does not prevent the one or more sensors from obtaining data.

In some implementations, the mobile device is a wearable device.

In some implementations, the mobile device is a watch.

In some implementations, the mobile device is a phone.

In some implementations, the mobile device is a monitoring hub.

In some implementations, transitioning the actuator between the first state and the second state causes the mobile device to transition between a privacy and a non-privacy mode.

In some implementations, the communication device includes a transceiver.

In some implementations, the communication device includes an antenna.

In some implementations, the communication device is configured to communicate via one or more wireless communication protocols.

In some implementations, the communication device is configured to communicate via one or more of Bluetooth, WiFi, cellular, Zigbee, Z-Wave, near-field communication (NFC), RFID, 1G, 2G, 3G, 4G, 5G.

In some implementations, the communication device is configured to transmit the sensor data to the one or more computing devices.

In some implementations, the actuator is disposed on a housing of the mobile device.

In some implementations, the actuator is a switch.

In some implementations, the actuator is a button.

Disclosed herein is a mobile device which may comprise: an actuator and one or more sensors. The actuator can be configured to cause the mobile device to transition between operation modes in response to actuation of the actuator, wherein during a privacy mode a power source of the mobile device is configured to disconnect from a communication device of the mobile device. The one or more sensors can be configured to generate sensor data during the privacy mode.

In some implementations, the operation modes include a privacy mode and a non-privacy mode.

In some implementations, the operation modes include a first privacy mode, a second privacy mode, and a non-privacy mode.

In some implementations, the actuator is dedicated to causing the mobile device to transition between operation modes.

In some implementations, the actuator is further configured only to cause the mobile device to transition between operation modes.

In some implementations, the mobile device is further configured to transition between operation modes in response to only the actuation of the actuator.

Disclosed herein is a system which may comprise: a wireless communications device. The wireless communications device may comprise: a health module and one or more processors. The health module may be configured to obtain or generate heath data from a user of the wireless communicates device. The one or more processors may be configured to implement a third party application, wherein implementing the third party application gives permission to the third party application to access the health data In some implementations, the system may further comprise a dedicated privacy switch implemented in hardware, wherein activation of the dedicated privacy switch causes the wireless communications device to prevent the third-party application from accessing the health data.

In some implementations, activation of the dedicated privacy switch causes the wireless communications device to prevent the third-party application from accessing the health data for a first period of time.

In some implementations, third party application is automatically allowed to resume accessing the health data after expiration of the first period of time.

In some implementations, the one or more processors are further configured to: associate an attribute with all of the health data obtained or generated by the health module; and in response to the activation of the dedicated privacy switch and during the first period of time, prevent transmission of or access to any data associated with the attribute.

In some implementations, the system is further configured to use metadata to tag health care data to associate an attribute with the health care data.

In some implementations, the health data is restricted by default, wherein a user can give permission to the third party application to access the health data.

In some implementations, the health data is restricted by default, wherein a user can give permission to sell the health data to the third party application, wherein the user shares in income from a sale of the health data.

In some implementations, to give permission to the third party application to sell or access the health data, the user can activate a hardware or software switch.

In some implementations, the health data is private, sensitive, confidential and/or HIPPA protected.

Disclosed herein is a mobile device which may comprise: a computer readable storage medium having program instructions embodied therewith; and one or more processors. The one or more processors can be configured to execute the program instructions to cause the mobile device to assign metadata to sensor data generated by one or more sensors of the mobile device based on whether the sensor data was generated during a privacy mode, wherein the privacy mode corresponds to a state of an actuator of the mobile device.

In some implementations, the one or more processors are further configured to execute the program instructions to cause the mobile device to: perform one or more operations based on the metadata of the sensor data.

In some implementations, the one or more operations includes communicating the sensor data to one or more remote devices.

In some implementations, assigning the metadata includes identifying whether the sensor data includes sensitive data.

In some implementations, the one or more processors are further configured to execute the program instructions to cause the mobile device to: assign the metadata during the privacy mode.

Disclosed herein is a mobile device which may comprise: a computer readable storage medium having program instructions embodied therewith; and one or more processors. The one or more processors can be configured to execute the program instructions to cause the mobile device to access first sensor data generated by one or more sensors of the mobile device during a privacy mode. The one or more processors can be configured to execute the program instructions to cause the mobile device to assign metadata to the first sensor data generated during the privacy mode to indicate the first sensor data includes sensitive data. The one or more processors can be configured to execute the program instructions to cause the mobile device to access second sensor data from the one or more sensors of the mobile device during a non-privacy mode. The one or more processors can be configured to execute the program instructions to cause the mobile device to assign metadata to the second sensor data received during the non-privacy mode to indicate the second sensor data includes non-sensitive data.

In some implementations, the one or more processors are further configured to execute the program instructions to cause the mobile device to: not delete the first sensor data received during the privacy mode.

In some implementations, the one or more processors are further configured to execute the program instructions to cause the mobile device to: store the first sensor data in storage.

In some implementations, the one or more processors are further configured to execute the program instructions to cause the mobile device to: store the first sensor data in a same or similar location in storage as the second sensor data.

In some implementations, the one or more processors are further configured to execute the program instructions to cause the mobile device to: communicate, via a communication device, the second sensor data; and not communicate, via the communication device, the first sensor data.

In some implementations, the one or more processors are further configured to execute the program instructions to cause the mobile device to: communicate, via a communication device, the second sensor data during a non-privacy mode; and not communicate, via the communication device, the first sensor data during the non-privacy mode.

Disclosed herein is a mobile device which may comprise: a computer readable storage medium having program instructions embodied therewith; and one or more processors. The one or more processors can be configured to execute the program instructions to cause the mobile device to receive sensor data from one or more sensors of the mobile device. The one or more processors can be configured to execute the program instructions to cause the mobile device to determine whether the sensor data was obtained by the one or more sensors during a privacy mode. The one or more processors can be configured to execute the program instructions to cause the mobile device to in response to determining that the sensor data was obtained from the one or more sensors during a privacy mode, assign metadata to the sensor data. The one or more processors can be configured to execute the program instructions to cause the mobile device to in response to determining that the sensor data was not obtained from the one or more sensors during a privacy mode, do not assign metadata to the sensor data.

In some implementations, the one or more processors are further configured to execute the program instructions to cause the mobile device to: determine whether the sensor data was obtained by the one or more sensors during a privacy mode based at least in part on a state of an actuator of the mobile device.

In some implementations, the one or more processors are further configured to execute the program instructions to cause the mobile device to: determine whether the sensor data was obtained by the one or more sensors during a privacy mode based at least in part on a state of a communication device of the mobile device.

Disclosed herein is a mobile device which may comprise: a computer readable storage medium having program instructions embodied therewith; and one or more processors. The one or more processors can be configured to execute the program instructions to cause the mobile device to access sensor data obtained from one or more sensors. The one or more processors can be configured to execute the program instructions to cause the mobile device to determine whether the sensor data was obtained during a privacy mode. The one or more processors can be configured to execute the program instructions to cause the mobile device to in response to determining that the sensor data was obtained during a privacy mode, do not communicate the sensor data to an external computing device. The one or more processors can be configured to execute the program instructions to cause the mobile device to in response to determining that the sensor data was not obtained during a privacy mode, communicate the sensor data to an external computing device.

In some implementations, the one or more processors are further configured to execute the program instructions to cause the mobile device to: in response to determining that the sensor data was obtained during a privacy mode, prevent a third-party application on the mobile device from accessing the sensor data.

In some implementations, the one or more processors are further configured to execute the program instructions to cause the mobile device to: in response to determining that the sensor data was not obtained during a privacy mode, allow a third-party application on the mobile device to access the sensor data.

Disclosed herein is a mobile device which may comprise: a computer readable storage medium having program instructions embodied therewith; and one or more processors. The one or more processors can be configured to execute the program instructions to cause the mobile device to generate user interface data for rendering a user interface. The one or more processors can be configured to execute the program instructions to cause the mobile device to display, via a display of the mobile device, a user interface. The user interface can include: an indication of time, one or more physiological parameters, and a privacy mode indication.

In some implementations, the one or more processors are further configured to execute the program instructions to cause the mobile device to: display the privacy mode indication when the mobile device is in a privacy mode.

In some implementations, the one or more processors are further configured to execute the program instructions to cause the mobile device to: display the privacy mode indication when the mobile device transitions to a privacy mode.

In some implementations, the one or more processors are further configured to execute the program instructions to cause the mobile device to: display the privacy mode indication when one or more communication devices of the mobile device are powered off.

In some implementations, the one or more processors are further configured to execute the program instructions to cause the mobile device to: display the privacy mode indication for a predetermined length of time after the mobile device transitions to a privacy mode.

In some implementations, the privacy mode indication is annular or semi-annular.

In some implementations, the privacy mode indication circumscribes the display of the mobile device.

In some implementations, the privacy mode indication circumscribes a watch face of the display.

In some implementations, the one or more processors are further configured to execute the program instructions to cause the mobile device to: display a second privacy mode indication at a same time as the privacy mode indication.

In some implementations, the one or more processors are further configured to execute the program instructions to cause the mobile device to: display the privacy mode indication for a predetermined length of time after the mobile device transitions to a privacy mode; and display the second privacy mode indication as long as the mobile device is in the privacy mode.

Disclosed herein is a mobile device which may comprise: a computer readable storage medium having program instructions embodied therewith; and one or more processors. The one or more processors can be configured to execute the program instructions to cause the mobile device to determine an operation status of one or more communication components of the mobile device. The one or more processors can be configured to execute the program instructions to cause the mobile device to determine an estimated amount of radio frequency energy to which a user of the mobile device is exposed. The one or more processors can be configured to execute the program instructions to cause the mobile device to display, via a display of the mobile device, an RF energy exposure indicator.

In some implementations, the one or more processors are further configured to execute the program instructions to cause the mobile device to: display, via the display of the mobile device, an operation status indicator.

In some implementations, the one or more processors are further configured to execute the program instructions to cause the mobile device to: adjust an operation of the one or more communication components.

In some implementations, the one or more communication components of the mobile device include a transceiver or a speaker.

In some implementations, the one or more communication components of the mobile device include a transceiver or a speaker.

In some implementations, the one or more processors are further configured to execute the program instructions to cause the mobile device to: determine the operation status of the one or more communication components based, at least in part, on an amount of power consumed by the one or more communication components.

In some implementations, the one or more processors are further configured to execute the program instructions to cause the mobile device to: determine the estimated amount of radio frequency energy to which a user of the mobile device is exposed based, at least in part, on the operation status of the one or more communication components.

In some implementations, the one or more processors are further configured to execute the program instructions to cause the mobile device to: determine the estimated amount of radio frequency energy to which a user of the mobile device is exposed based, at least in part, on detected RF energy emitted from one or more communication devices remote to the mobile device.

In some implementations, the one or more communication devices is a base station.

In some implementations, the RF energy exposure indicator indicates an amount of RF energy to which the user is exposed.

In some implementations, the RF energy exposure indicator indicates whether the user is exposed to a threshold amount of RF energy.

In some implementations, adjusting the operation of the one or more communication components includes turning off a transceiver of the mobile device.

In some implementations, adjusting the operation of the one or more communication components includes turning on a speaker of the mobile device.

In some implementations, the operation status indicator indicates whether the one or more communication components are powered on or off.

Disclosed herein is a method for adjusting a radiofrequency (RF) energy emitted by a mobile device. The method can comprise: based at least in part on a determination that a first condition is satisfied, adjusting at least one setting of the mobile device to reduce an amount of RF energy emitted by the mobile device.

In some implementations, the first condition corresponds to a cellular signal strength.

In some implementations, the first condition is satisfied when the cellular signal strength does not satisfy a threshold signal strength.

In some implementations, the first condition is satisfied when the cellular signal strength is less than the threshold signal strength.

In some implementations, the method may further comprise determining the cellular signal strength corresponding to the mobile device.

In some implementations, the threshold signal strength is less than at least one of −50 dBm, −80 dBm, −90 dBm, −100 dBm, or −110 dBm.

In some implementations, the first condition corresponds to audio output settings of the mobile device.

In some implementations, the first condition is satisfied when the audio output settings indicate audio output through an embedded of the mobile device.

In some implementations, the first condition is not satisfied when the audio output settings indicate that the mobile device is configured to output its audio through a speaker external to the mobile device.

In some implementations, the first condition is not satisfied when the audio output settings indicate that the mobile device is configured in a speakerphone mode.

In some implementations, the first condition corresponds to a user-editable setting.

In some implementations, the first condition is satisfied when the user-editable setting is activated by the user.

In some implementations, the at least one setting comprises an RF transmission power of the mobile device.

In some implementations, the at least one setting comprises a network mode.

In some implementations, the network mode comprises at least one of 2G, 3G, 4G, or 5G.

In some implementations, the network mode comprises at least one of GSM, CMDA, LTE/CDMA, or LTE.

In some implementations, adjusting the at least one setting comprises enabling at least one of 2G, 3G, 4G, or 5G.

In some implementations, adjusting the at least one setting comprises disabling a different one of the at least one of 2G, 3G, 4G, or 5G.

Disclosed herein is a mobile communications device having configurable radiofrequency (RF) energy emissions. The mobile communications device can comprise: a communication interface and one or more processors in communication with the communication interface. The communications interface can comprise at least a transceiver and an antenna. The communications interface can be configured to enable wireless communication for the mobile communications device using one or more radio bands. The one or more processors can be configured to, based at least in part on a determination that a first condition is satisfied, adjust at least one setting of the mobile communications device to reduce an amount of RF energy emitted by the communication interface.

In some implementations, the first condition corresponds to a cellular signal strength.

In some implementations, the first condition is satisfied when the cellular signal strength does not satisfy a threshold signal strength.

In some implementations, the first condition is satisfied when the cellular signal strength is less than the threshold signal strength.

In some implementations, the threshold signal strength is less than at least one of −50 dBm, −80 dBm, −90 dBm, −100 dBm, or −110 dBm.

In some implementations, the first condition corresponds to audio output settings of the mobile communications device.

In some implementations, the first condition is satisfied when the audio output settings indicate audio output through an embedded of the mobile communications device.

In some implementations, the first condition is not satisfied when the audio output settings indicate that the mobile communications device is configured to output its audio through a speaker external to the mobile communications device.

In some implementations, the first condition is not satisfied when the audio output settings indicate that the mobile communications device is configured in a speakerphone mode.

In some implementations, the first condition corresponds to a user-editable setting.

In some implementations, the first condition is satisfied when the user-editable setting is activated by the user.

In some implementations, the at least one setting comprises an RF transmission power of the communication interface.

In some implementations, the at least one setting comprises a network mode.

In some implementations, the network mode comprises at least one of 2G, 3G, 4G, or 5G.

In some implementations, the network mode comprises at least one of GSM, CMDA, LTE/CDMA, or LTE.

In some implementations, adjusting the at least one setting comprises enabling at least one of 2G, 3G, 4G, or 5G.

In some implementations, adjusting the at least one setting comprises disabling a different one of the at least one of 2G, 3G, 4G, or 5G.

In some implementations, adjusting the at least one setting cellular data.

In some implementations, the mobile communications device can further comprise a privacy switch.

In some implementations, the privacy switch allows a user to disconnect or disable at least one of a camera, microphone, speaker, display, GPS system, Wi-Fi system, cellular data system, a third-party application, communication with third-party applications, an application that shares or requests health data.

BRIEF DESCRIPTION OF THE DRAWINGS

Various aspects will be described hereinafter with reference to the accompanying drawings. These aspects are illustrated and described by example only, and are not intended to limit the scope of the disclosure. In the drawings, similar elements have similar reference numerals.

DETAILED DESCRIPTION

Figure 1A:
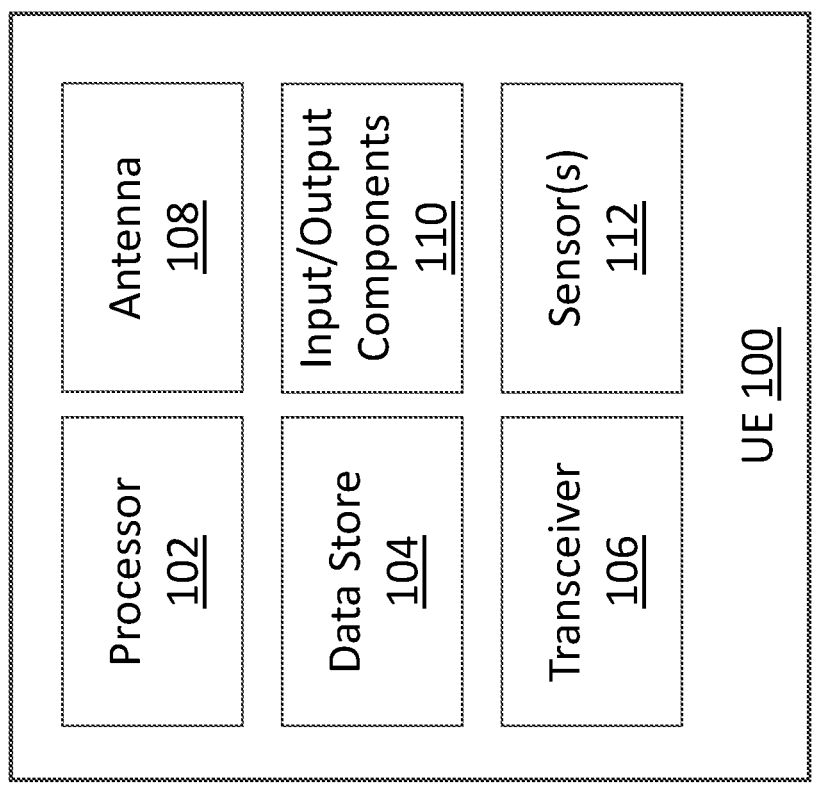
FIG. 1A illustrates a block diagram of an example mobile device.

Although certain aspects and examples are described below, those of skill in the art will appreciate that the disclosure extends beyond the specifically disclosed aspects or uses and obvious modifications and equivalents thereof. Thus, it is intended that the scope of the disclosure herein disclosed should not be limited by any particular aspects described below.

Introduction

Mobile devices, such as mobile phones, watches, laptops, tablets, earbuds, or the like, may be used for mobile communications over a network or directly between devices. For example, a mobile device can convert voice, text, multimedia messages or data calls into radio frequency (RF) signals and can transmit those RF signals to (or receive RF signals from) one or more remote communication devices, which can connect to other mobile devices or networks.

While in use, a mobile device (sometimes referred to as a mobile communications device) may emit levels of non-ionizing radiation, generally referred to as RF energy. The exposure to RF energy emitted from these and other devices has led to concerns about the potential health effects to cognitive function, memory, sleep, or heart-rate, to name a few, as well as concerns regarding an increased risk of cancer, tumors, migraines, etc. As a result, there is a desire to reduce exposure to and/or limit the generation of RF energy produced by mobile devices.

To reduce undesired exposure to RF energy, the mobile device may be implemented with dynamically adjustable or user-controllable parameters relating to RF energy emitted by the mobile device. By enabling these modifications, the emitted RF energy can be tuned to a "safe" or desired level, which can vary based on the user's objective or subjective risk tolerance. In some cases, reducing the RF energy emitted by the mobile device may also reduce communication capabilities of the mobile device. Thus, by enabling these modifications, the mobile device advantageously allows a user to select what is important at a given time: reduced RF exposure or increased communication capabilities.

In some cases, the parameters relating to RF energy emitted by the mobile device can be dynamically adjusted by the mobile device based on the presence of one or more conditions. As an example, the mobile device may be configured to analyze the signal strength and quality (sometimes referred to as reception) of a remote communication device. Remote communication devices, as used herein, can include one or more various devices configured to wirelessly communicate such as base stations (which may also be referred to as cell towers), routers, cellphones, computers, monitors, sensors, and/or the like. Depending on various factors, such as proximity of a mobile device to a remote communication device, obstructions by buildings or trees, weather, etc. the signal strength and quality can vary. In some cases, the mobile device can use a signal strength and quality threshold to determine whether to adjust its settings. For example, if the signal strength and quality of the mobile device with a particular remote communication device does not satisfy the signal strength and quality threshold, then the mobile device may determine to at least temporarily reduce or turn off its RF communications with that particular remote communication device, which can reduce the RF energy emitted by the mobile device and/or the user's exposure to RF energy.

One example of the features described herein includes signal strength and quality-triggered control of the mobile device. For example, based on a failure to satisfy a connectivity threshold (for example, a signal strength and quality threshold), the mobile device may automatically adjust one or more connectivity parameters (for example, Wi-Fi capabilities, cellular data capabilities, RF transmission power, enabled or disabled networks (for example, 2G, 3G, LTE, 4G, 5G, etc.)) to reduce an amount of RF energy emitted by the mobile device. Accordingly, in some cases, the mobile device may be configured to sacrifice at least some degree of communication in favor of reduced exposure to RF energy.

Typically, exposure to RF energy decreases as a user moves away from the source. However, those mobile device that involve close distances between a user and the mobile device can make it difficult for the user to keep a distance between themselves and the mobile device. For example, in a situation in which a user holds a cell phone to their ear during use, RF energy emitted by the antenna may be absorbed in high concentrations at the head region of the user. In some cases, placing the cell phone in speaker mode or connecting a remote speaker (for example, Bluetooth speaker, ear buds, head phones, etc.) can provide an opportunity for the user to place a larger distance between the user and the source of the RF energy, which may reduce the user's exposure to RF energy.

Another example of the features described herein includes audio output-triggered control of the mobile device. For example, in some cases, based on an audio output configuration of the mobile device, the mobile device may automatically adjust one or more connectivity parameters to reduce an amount of RF energy emitted by the mobile device. For example, based on a determination that the mobile device is configured to output audio through a speaker of the mobile device (for example, in a non-speakerphone mode), the mobile device may be configured to at least temporarily reduce or turn off its RF communications with the remote communication device (for example, by turning off cellular data, Bluetooth or Wi-Fi, decreasing RF transmission power, etc.). As a corollary, based on a determination that the mobile device is configured to output audio through an external or remote speaker (for example, headphones, earbuds, vehicle speaker, portable speaker, etc.) and/or using a speakerphone mode of the mobile device, the mobile device may be configured to retain default communication settings, because under such settings the user may be a further distance from the mobile device. Accordingly, in some cases, the mobile device may be configured to adjust an emission of RF energy based on a distance, or expected distance, of the user from the mobile device.

Yet another example of the features described herein includes a healthcare-focused mobile device. For example, the mobile device may include cellular data capabilities, but may limit use to connections with health care workers, caregivers, family, etc. Furthermore, the mobile device may allow for modifications of parameters relating to RF energy emitted by the mobile device, as described herein. Furthermore, the mobile device may be configured to provide appointment or medication reminders, facilitate prescription pickups, provide a medical alert button, include games for challenging or training your brain, etc. Furthermore, the mobile device may be configured to include, connect to, or communicate with one or more physiological sensors, such as optical sensors with light emission and detection circuitry, acoustic sensors, devices that measure blood parameters from a finger prick, pulse oximeters, or one or more sensors produced by Masimo Corporation, Irvine, CA. In this way, the mobile device provides a single device for some, most, or all of a user's healthcare needs. Furthermore, by limiting the capabilities of the mobile device to largely healthcare related functions, the mobile device advantageously limits the complexities of using a mobile device, while also providing a means of potentially reducing undesired exposure to RF energy.

Another independent feature described herein is a privacy switch that allows selective deactivation of select components of the mobile device. In particular, the mobile device can include one or more privacy switches that can disconnect or disable components of the mobile device that are tied to a user's privacy. For example, a privacy switch may allow a user to disconnect or disable one, some, or all of a camera, microphone, GPS system, Wi-Fi system, cellular data system, communication with third-party applications, any application that shares or requests health data, etc. In some cases, the switch can sever a physical connection between one or more privacy components of the mobile device and a power source and/or processor of the mobile device, making the privacy component(s) inaccessible to the mobile device or remote systems. Privacy components can include communication devices such as transceivers, visual displays such as screens, audio output such as speakers, GPS/GNSS, memory units storing sensitive data, physiological monitors or the like. In some cases, the switch can, in addition or alternatively, authorize or deauthorize communication of health data. For example, the switch may be configured to remove any previously granted permissions associated with some or all applications (for example, third party applications) or privacy components. In some cases, the switch can be implemented in hardware, thereby allowing easy recognition of whether the switch is in the on or off position. In some cases, the switch can be implemented in software. The privacy features and the RF features described above and throughout this Application can both be included in the same mobile device or can independently be included.

Example System Overview

FIG. 1A illustrates a block diagram of an example mobile device 100. In this example, the mobile device 104 includes a processor 102, a data store 104, a transceiver 106, antenna 108, input and output components 110, and one or more sensors 112. The mobile device 100 can be implemented as a cell phone, smart phone, tablet computer, desktop computer, laptop, mobile computing device, mobile phone, personal digital assistant (PDA), hybrid PDA/mobile phone, any electronic device configured to communicate over a network (non-limiting examples: a cellular network or other wireless network, or wired network), or any device configured for the internet of things. The mobile device 100 can include fewer, additional, or different components. For example, in some cases, the mobile device 100 includes an emitter and a detector for obtaining one or more physiological measurements.

The data store 104 (for example, non-transitory computer-readable media) can include computer-executable instructions that when executed by the processor 102 cause the processor 102 to perform a number of functions, programs, applications, and/or services. In some cases, the data store 104 can include a user interface module, a signal processing module, or configuration parameters. In some cases, the data store 104 can be used to store information about operation of the mobile device 100. This information can, for example, include readouts of measures or parameters, trends and bar graphs of measures or parameters, visual indications or indicators.

The mobile device 100 can include a communication interface, such as a transceiver 106 that includes an antenna 108, for wireless communication using one or more radio bands. As described, the mobile device 100 may communicate with one or more remote communication devices. For example, the transceiver 106 can transmit voice, text, multimedia messages or data calls as RF signals to one or more base stations. The transceiver 106 can receive RF signals as well. As described herein, the RF signals transmitted by the communication interface can be based at least in part on a transmitter power output and power gain. In some cases, the transceiver 106 can transmit information about operation of the mobile device 100 to an electronic device or receive control or configuration data for operating the mobile device 100. In some case, the transceiver 106 can communicate via a computer network or intermediary device or directly with the electronic device using electromagnetic radiation or other wireless communication (for example, Bluetooth, Wi-Fi, etc.). The input and output components 110 can include one or more devices like a keypad, touch screen, pointing device, voice recognition device, audio controls, power controls, etc.

As described herein, in some cases, a mobile device 100 may include or be configured to communicate with one or more sensors 112. For example, the mobile device 100 may be configured to include, connect to, or communicate with one or more optical sensors with light emission and detection circuitry, acoustic sensors, devices that measure blood parameters from a finger prick, pulse oximeters, or one or more sensors produced by Masimo Corporation, Irvine, CA.

Figure 1B:
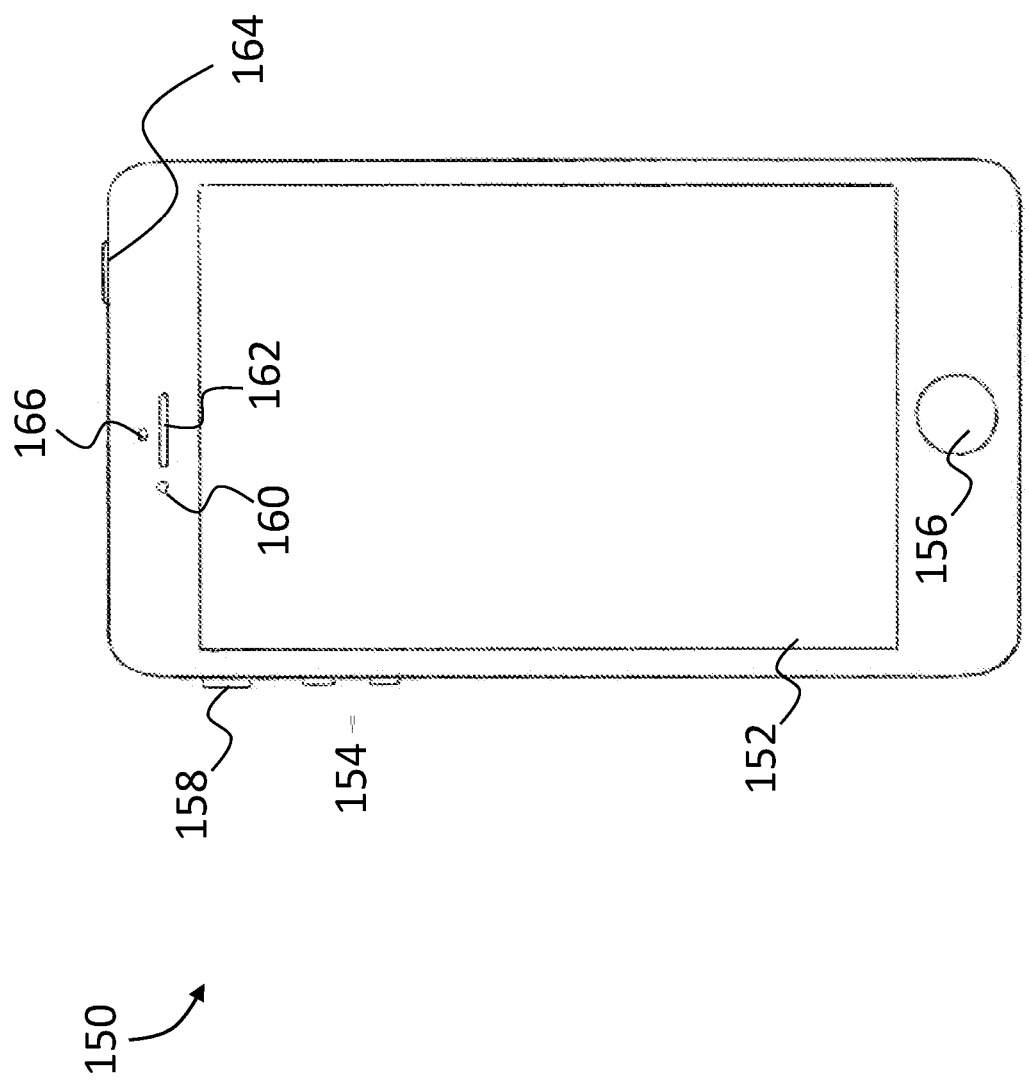
FIG. 1B illustrates a perspective view of an example mobile device implemented as a cell phone.

FIG. 1B illustrates a perspective view of an example mobile device 150 implemented as a cell phone. The mobile device 150 can be an aspect of the mobile device 100 of FIG. 1A. In this example, the mobile device 150 includes a display/touch screen 152, audio control 154, a control button 156, a microphone 166, a camera 160, and a speaker 162. It will be understood that the mobile device 150 can include fewer, additional, or different components. As described, in some cases, the mobile device 150 may be healthcare-focused. For example, the mobile device 150 may include cellular data capabilities, but may limit cellular use to communications with health care workers, caregivers, family, etc. By limited communications, the mobile device 150 may reduce RF energy emissions as compared to mobile device that do not have its communications limited. Further, mobile device may allow for modifications of parameters relating to RF energy emitted by the mobile device 150, as described herein. Furthermore, the mobile device may be configured to provide appointment or medication reminders, facilitate prescription pickups, provide a medical alert button, include games for challenging or training your brain, etc.

The mobile device 150 also includes a privacy switch 158 that can facilitate the protection of a user's data. Example implementations of a privacy switch are described in greater below.

The mobile device 150 also includes a pairing button 164, which can facilitate connection between the mobile device 150 and one or more sensors (for example, one or more sensors developed by Masimo Corporation, Irvine, CA). The pairing button 164 can be used to connect a sensor or other devices to the mobile device 150. Once pairing is complete, the mobile device 150 can communicate with and/or control the paired device.

Figure 2:
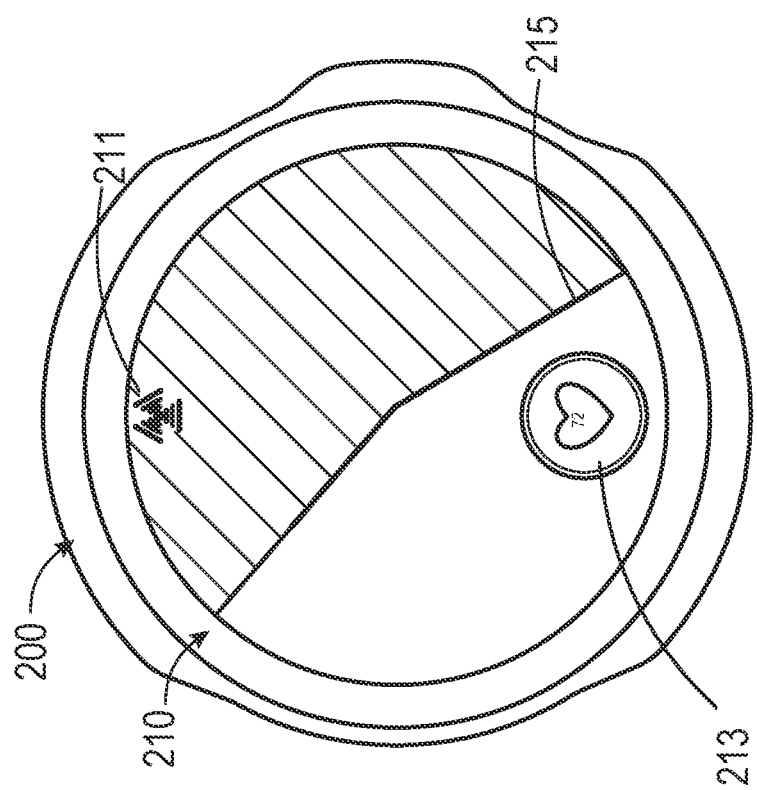
FIG. 2 illustrates an example display of a mobile device which may display RF related data.

FIG. 2 illustrates an example display 210 of a mobile device 200 which may display a user interface. The mobile device 200 may be a watch. In some implementations, the mobile device 200 may be a phone. Display 210 can display time 215, such as an analog watch face, sensor data 213, including physiological parameters such as heart rate, and an electromagnetic indicator 211. The electromagnetic indicator 211 may indicate whether a threshold level of radiation is detected by the mobile device. The electromagnetic indicator 211 may indicate whether electromagnetic interference (EMI) is detected by the mobile device. The electromagnetic indicator 211 may indicate whether radio frequency (RF) radiation is detected by the mobile device. The electromagnetic indicator 211 may indicate an amount of radio frequency (RF) radiation generated by the mobile device 200. The electromagnetic indicator 211 may indicate to a user whether the user is being exposed to radiation, such as RF radiation, which may be harmful to the user. The electromagnetic indicator 211 may indicate an amount of RF energy to which the user is exposed and/or whether the amount of RF energy to which the user is exposed exceeds a threshold. The electromagnetic indicator 211 may indicate a mode of operation of the mobile device. For example, the electromagnetic indicator 211 may indicate whether the mobile device has temporarily reduced or turned off any of its communication devices, including devices that emit RF energy such as transceivers, to reduce the RF energy emitted by the mobile device and/or the user's exposure to RF energy.

Figure 3:
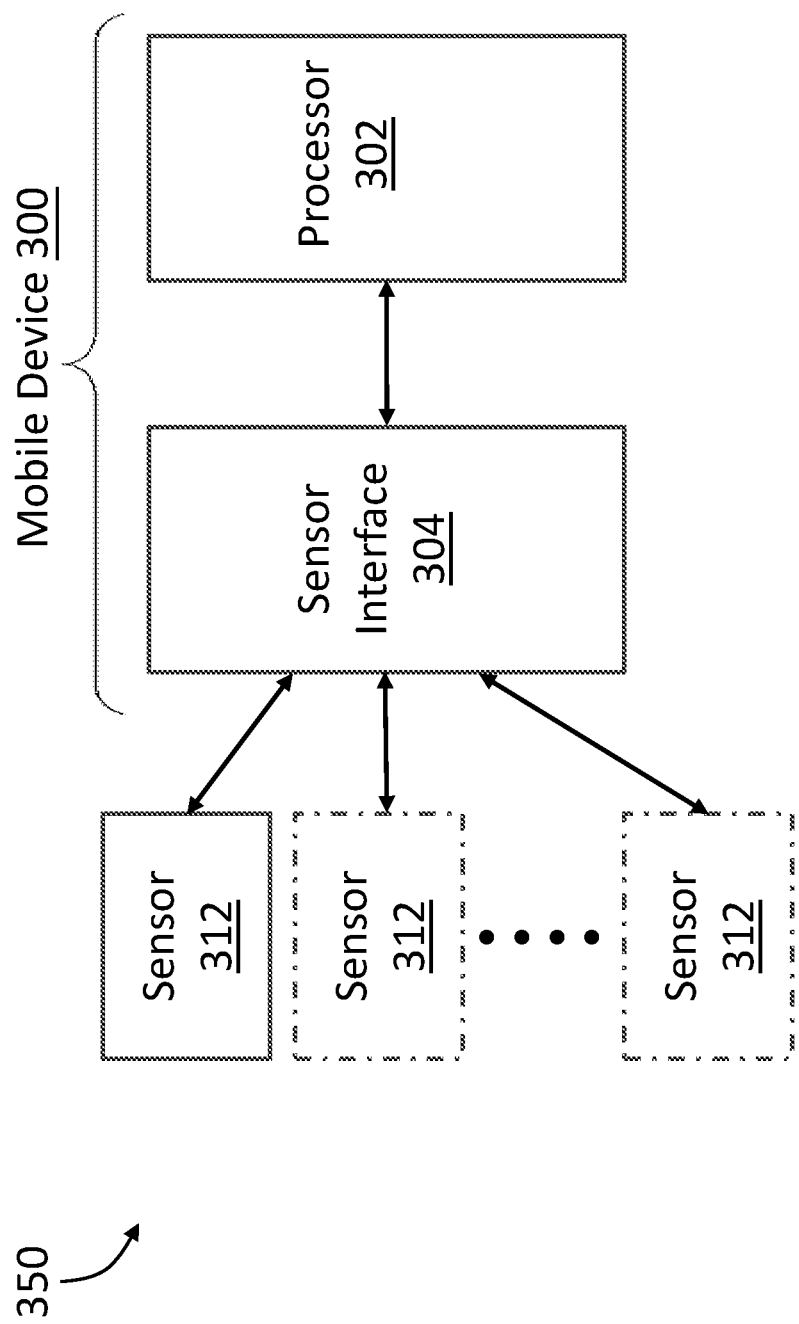
FIG. 3 illustrates an example patient monitoring system that includes a mobile device and a sensor.

FIG. 3 illustrates an example patient monitoring system 350 that includes a mobile device 300 and a sensor 312. The sensor 312 can generate sensor data relating to a blood constituent, a blood analyte, or a physiological parameter. The mobile device 300 can obtain sensor data from the sensor 312 and can determine one or more physiological parameters based on the sensor data. It will be understood that the patient monitoring system 300 may include any number of sensors of the same or a different type.

The mobile device 300 can include a sensor interface 304 and a processor 302. The sensor 312 can provide a stream of data to processor 302. For example, the sensor 312 can be connected to the sensor interface 304 via a wired or wireless connection. An output of the sensor interface 304 can be fed into the processor 302 in a raw or partially processed data form. Partially processed sensor data can be demodulated, filtered, or otherwise processed to prepare the data for use by the processor 302 to calculate measurements of physiological parameters. Partially processing the sensor data can include generating basic ratios of wavelengths in a multi-wavelength system. The processor 302 can include one or more hardware or software signal processors. Partial processing can include, for example, a low or high pass filter or other preprocessing steps typically performed in a signal acquisition system.

The unprocessed or partially processed streams of data from the sensor 312 can be combined by the processor 302 into combined sensor data. The combined sensor data can include a plurality of features of the signals from the sensor 312, such as amplitude, phase, AC value, DC value, or others. Measurement site or body tissue information can be provided to the processor 302 as independent features. The processor 302 can produce one or more measurements of a physiological parameter based on the combined sensor data. The plurality of features of the signals can be mapped onto empirical data, which can provide estimates of physiological parameter measurements. The additional independent features of the measurement site or body tissue information can provide more combinations of features and improve the estimation of the physiological parameters. The combinations of features can be linear or can include high-ordered combinations. The processor 302 can analyze from the combined sensor data various features, such as a ratiometric value, such as ratios of attenuated light of one wavelength to attenuated light of another wavelength, or combinations of features, including non-normalized features, data from bulk absorption or peripheral absorption signals, or others. The physiological parameter can include, but is not limited to, total hemoglobin (SpHb®, oxygen saturation (SpO$_2$), pulse rate, a plethysmograph waveform, perfusion index (PI), PPR, SV, MAP, CVP, PP, PI, pleth variability index (PVI®), methemoglobin (MetHb), carboxyhemoglobin (CoHb), total hemoglobin (tHb), glucose, absorbance, hydration index, path length, etc. or any combination thereof. etc.

Figure 4:
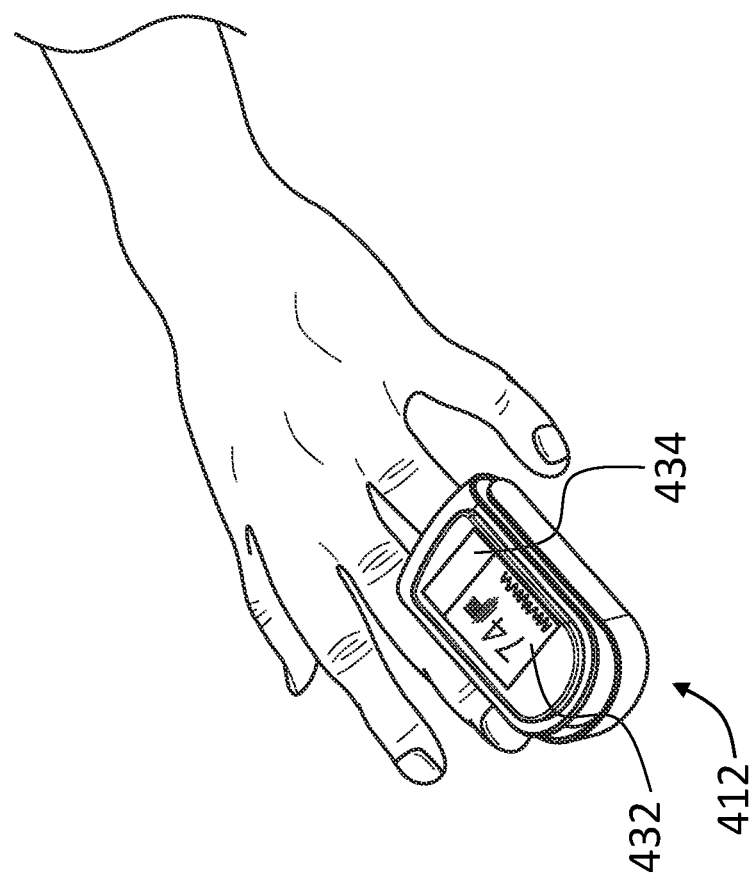
FIG. 4 illustrates an environment that includes an example mobile device and an example patient sensor device.
Figure 4:
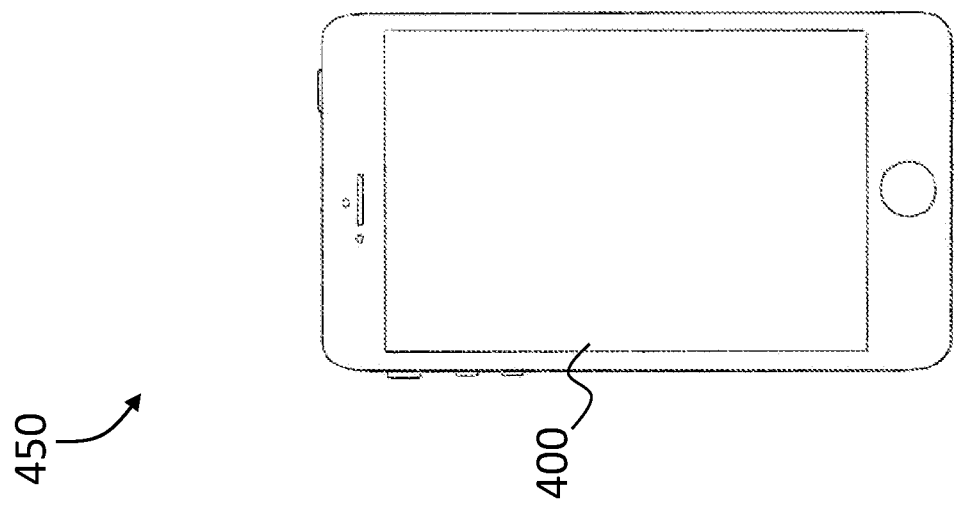

FIG. 4 illustrates an environment 450 that includes an example mobile device 400 and an example patient sensor device 412. The patient sensor device 412 can be an aspect of the sensor 112 of FIG. 1A or the sensor 312 of FIG. 3. As described, the mobile device 400 can wirelessly communicate (for example, over Bluetooth, Wi-Fi, cellular, etc.) with one or more patient sensor devices 412. The mobile device 400 can communicate with the patient sensor device 412 to obtain patient data, such as captured patient physiological data.

The patient sensor device 412 can be a pulse oximeter that is designed to non-invasively monitor patient physiological parameters from a fingertip. The patient sensor device 412 can include a display/touchscreen 432 and/or a touchpad 434. Example physiological parameters that the patient sensor device 412 can measure can include, but is not limited to, blood oxygen saturation, pulse rate, perfusion index, respiration rate, hydration index, and/or pleth variability index. The patient sensor device 412 can be implemented as a MightySat® fingertip pulse oximeter by Masimo Corporation, Irvine, CA Other example patient sensor devices 412 can include, but are not limited to, a tetherless pulse oximetry sensor/pulse oximetry device with respiration rate monitoring or a device capable of administering one or more medications.

Example Flow Diagrams

Figure 5A:
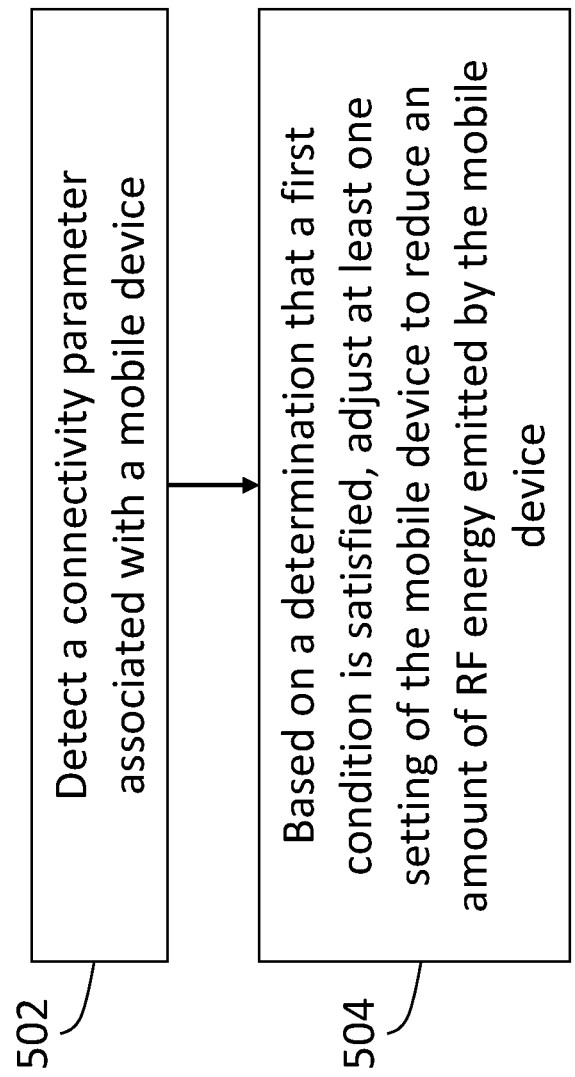
FIG. 5A is a flow diagram illustrative of an aspect of a routine implemented by a mobile device for modifying RF energy emitted by the mobile device.

FIG. 5A is a flow diagram illustrative of an aspect of a routine implemented by a mobile device for modifying RF energy emitted by the mobile device. One skilled in the relevant art will appreciate that the elements outlined for routine 500 may be implemented by one or many computing devices/components, such as the processor 102 of mobile device 100. For ease of reference, routine 500 has been logically associated as being generally performed by the mobile device 100. However, the following illustrative aspects should not be construed as limiting.

At block 502, the mobile device 100 detects or determines one or more connectivity parameters associated with the mobile device 100. The one or more connectivity parameters can vary across aspects. In certain aspects, the connectivity parameter relates to the signal strength and/or quality of mobile device with a remote communications device such as a base station. Remote communication devices, such as base stations, can routinely broadcast information in the form of broadcast signals or messages over one or more frequency bands within a coverage area. The information can be broadcast multiple times a second and can include bandwidth information for the remote communication device at a particular frequency band, signal decoding information that can be used to decode future signals and symbols, system frame timing, etc. This information can enable mobile device 100 within the coverage area to determine the signal strength or quality of the remote communication device.

In certain aspects, the connectivity parameter relates to an audio output setting of the mobile device 100. As described herein, the mobile device 100 may include one or more speakers, which in some cases may be set to speakerphone mode or non-speakerphone mode. Furthermore, the mobile device 100 may be configured to connect to one or more external speakers through a wired or wireless connection (for example, Bluetooth speaker, Wi-Fi speaker, head phones, ear buds, etc.). In some cases, the connectivity parameter includes an indication of the audio output setting, such as whether the speakerphone mode is enabled or disabled, or whether the mobile device 100 is set to output its audio through an external speaker.

In certain aspects, the connectivity parameter relates to user input. For example, the connectivity parameter can be tied to a user editable setting, such as "airplane mode" or whether cellular data is activated. In this way, in some cases, the user can be in control of the connectivity parameter.

At block 504, the mobile device 100 adjusts at least one parameter relating to RF energy emitted by the mobile device. In certain aspects, the adjustment of the parameter results in a reduced specific absorption rate (SAR) value associated with the mobile device 100. The SAR is a measure of the rate of RF energy absorption by the body from the source being measured. SAR can provide a straightforward means for measuring the RF exposure characteristics of mobile device, for example to ensure that they are within the safety guidelines set by the FCC. In certain aspects, the adjustment of the parameter results in the RF energy having an altered frequency (for example, lower frequency), wavelength, power, etc.

The at least one parameter can vary across aspects. For example, the parameter can include, but is not limited to, transmitter power output, power gain, frequency, wavelength, network (for example, 2G, 3G, 5G, 5G, etc.), airplane mode, or cellular data activation. The RF energy produced by the mobile device 100 can be based at least in part on the transmitter power output or the power gain, among other factors. In some aspects, the at least one parameter relating to RF energy emitted by the mobile device includes the transmitter power output or the power gain. For example, a decrease in the transmitter power output or the power gain may result in a reduced RF energy. As a corollary, an increase in the transmitter power output or the power gain may result in an increase RF energy.

The RF energy produced by the mobile device 100 has a frequency and a wavelength. In certain aspects, the at least one parameter relating to RF energy emitted by the mobile device includes the frequency or wavelength of the RF energy or the RF signals. For example, a decrease in the frequency may result in a reduced RF energy, while an increase in the frequency may result in an increase RF energy.

In some aspects, the mobile device 100 is configured for any of various networks. For example, the mobile device 100 may be selectably configured for 1G, 2G, 3G, 4G, 5G, or any other generation of cellular network technology. For example, the mobile device 100 may include hardware for two or more generations. In some cases, one generation of technology may produce greater RF energy than another generation. For example, the higher frequency of 5G may produce more RF energy than any of 2G, 3G, or 4G. In some aspects, the at least one parameter includes a network parameter which correspond to the activated network (for example, 1G, 2G, 3G, 4G, 5G, etc.). For example, in some cases, the mobile device 100 may adjust the at least one parameter to switch from one wireless protocol to another. For example, the switch can be from 5G to 4G, 4G to 3G, etc., which may affect the emission of RF energy by the mobile device 100. Similar, in some cases, the mobile device 100 may adjust the at least one parameter to switch from one of GSM, CMDA, LTE/CDMA, or LTE or a different one of GSM, CMDA, LTE/CDMA, or LTE.

In some aspects, the mobile device 100 adjusts at least one parameter based on a determination that a condition is satisfied. The condition can correspond to user input, such as the user toggling a hardware or software switch. For example, in some cases, the first condition is satisfied when the user turns off cellular data, turns on airplane mode, or otherwise indicates an intention or reduce RF energy.

In some cases, the condition can correspond to the connectivity parameter and the condition may be satisfied when the connectivity parameter satisfies a connectivity threshold. As an example, in some cases, the condition can be satisfied when a signal strength and quality satisfies a signal strength and quality threshold. For example, the mobile device 100 can be configured to analyze the signal strength and quality of remote communication devices such as base stations. In some cases, the mobile device 100 can determine that the condition is satisfied if the signal strength and/or quality between the mobile device and a particular remote communication device exceeds a signal strength and/or quality threshold. In some cases, the mobile device 100 can determine that the condition is not satisfied if the signal strength and/or quality between the mobile device and a particular remote communication device does not exceed a signal strength and/or quality threshold. The signal strength and/or quality threshold can vary. For example, in some cases, the signal strength and/or quality threshold may be measured in decibel-milliwatts and can be at least one of −50 dBm, −80 dBm, −90 dBm, −100 dBm, or −110 dBm (+/− a few dBm). In some cases, the signal strength and/or quality threshold can correspond to a particular signal strength and/or quality level that is sufficient to enable communications between the mobile device 100 and the remote communication device.

As another example, in some cases, the connectivity parameter can correspond to audio output settings. For example, in some cases, the condition can be satisfied when a certain audio output settings are configured. For example, in some cases, the condition is satisfied when a speaker of the mobile device is configured in a speakerphone mode. As another example, in some cases, the condition is satisfied when mobile device 100 is set to output its audio through an external speaker.

Depending on the aspect, certain acts, events, blocks, or functions of any of the routine 500 can be performed in a different sequence, can be added, merged, or left out altogether (non-limiting example: not all described operations or events are necessary for the practice of the routine 500). In certain aspects, operations or events can be performed concurrently rather than sequentially.

Figure 5B:
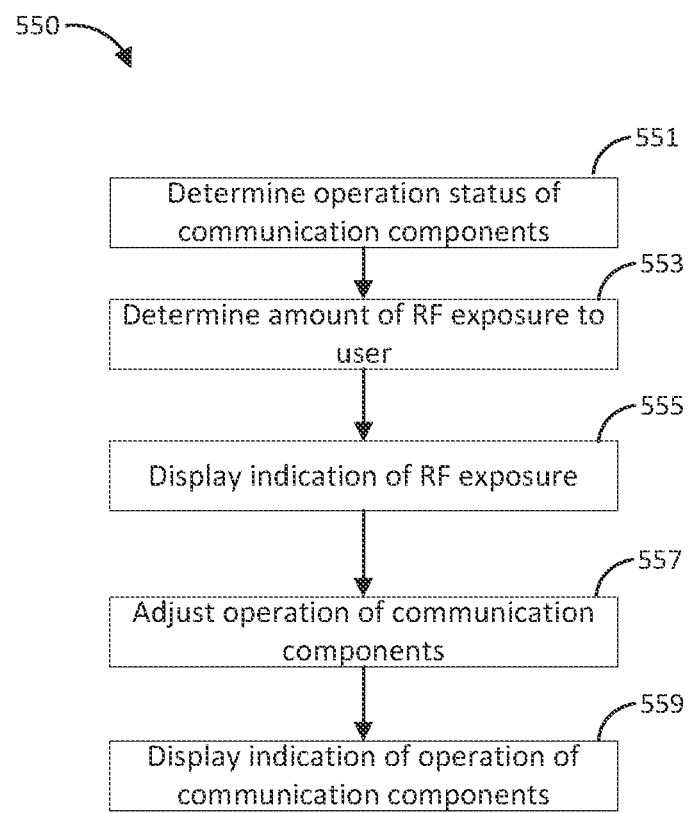
FIG. 5B is a flowchart illustrating an example process for determining RF exposure to a user of a mobile device.

FIG. 5B is a flowchart illustrating an example process 550 for determining RF exposure to a user of a mobile device. The process 550, or portions thereof, can be implemented on a mobile device and executed by one or more hardware processors. In some implementations, the process 550, or portions thereof, can be performed by the processor 102 described herein. Process 550 is provided as an example and is not intended to be limiting of the present disclosure. In some implementations, the mobile device may omit portions of the process 550, may add additional operations, and/or may rearrange an order of the operations shown.

At block 551, a mobile device (or hardware processor thereof), such as any of the example mobile devices shown and/or described herein may determine an operation status of one or more communication components of the mobile device. Communication components can include hardware devices configured to facilitate communication of the mobile device with remote communication devices. Communication components can include, for example, transceivers configured to communicate via one or more wireless communication protocols such as WiFi, Bluetooth, near field communication (NFC), radio frequency identification (RFID), cellular, 1G, 2G, 3G, 4G, 5G, Zigbee, Z-wave, and/or the like. Communication components can include speakers configured to output an audio signal of the communication data received from a remote communication device.

Determining an operation status can include determining whether the communication components are turned on and/or receiving power. Determining an operation status can include determining an amount of power being consumed by the communication components. Whether the communication components are power on and/or the amount of power they are consuming can indicate an amount of RF energy the communication components are emitting. As an example, if a transceiver is powered on, the transceiver may be emitting RF energy and exposing a user of the mobile device to high amounts of RF energy. As another example, if a speaker is powered on and/or consuming large amounts of power, a user of mobile device may be listening to audio from the mobile device at a distance and may be exposed to lower amounts of RF energy than if the speaker were off and the user were listening to audio at a closer distance.

At block 553, the mobile device may determine an amount of RF energy to which a user of the mobile device is exposed. The mobile device may determine the amount of RF exposure based, at least in part, on the determination at block 551. The determination of RF exposure may be an estimation. In some implementations, the mobile device may determine the RF exposure based, at least in part, on detecting one or more remote communication devices in proximity to the mobile device such as be detecting RF energy emitted by the one or more remote communication devices.

At block 555, the mobile device can display an indication of RF exposure to the user of the mobile device. The mobile device can display a binary representation that the user is being exposed to greater than a threshold amount of RF energy or less than a threshold amount of RF energy. The mobile device can display an indication of an amount of RF energy to which the user is estimated to be exposed.

At block 557, the mobile device can adjust an operation of the communication components of the mobile device. In some implementations, the mobile device may adjust the operation automatically based, at least in part, on the determination at block 553. For example, if the mobile device determines that an estimated RF exposure to a user exceeds a threshold, the mobile device may turn off one or more communication components, such as a transceiver. As another example, if the mobile device determines that an estimated RF exposure to a user exceeds a threshold, the mobile device may turn on a speaker to induce a user to listen to audio at a distance from the mobile device. In some implementations, the mobile device may adjust the operation based, at least in part, in response to a user input. For example, a user may authorize a suggested operation adjustment. As another example, a user may request specific adjustment to operation, such as in response to viewing the RF exposure displayed by the mobile device at block 555.

At block 559, the mobile device may display an indication of the operation status of the communication components of the mobile device. For example, the mobile may display an indication that the mobile device has powered off a transceiver of the mobile device.

Privacy

A dedicated privacy button for mobile device or wireless communications device (for example, cell phone, smart watch, etc.) can permit a user to control if and/or when third party apps, such as apps downloaded from an app store) are allowed to access private or sensitive data, such as health data. Some legitimate third party apps are given permission (for example, by the user) to access a user's health data via an API. However, the permission is typically "all or nothing." Disclosed herein is a dedicated privacy button (for example, a hardware switch, a software switch, etc.) that allows a user to activate a privacy window (for example, a particular duration of time) over which little or no health data is shared (for example, with any apps, or with a particular app). Disclosed herein is a mobile device that includes software, firmware, hardware, or any combination thereof to provide or facilitate healthcare related services or applications. The mobile device may include hardware or software configurations that allows a user to adjust privacy-related settings, for example restricting sensitive and personal data.

A mobile device can include a health module and one or more processors. The mobile devices can be an aspect of the mobile device 100, 150, or 300 of FIGS. 1A, 1B, or 3, respectively, and/or include one or more features or components thereof. For example, the mobile device can be implemented as a cell phone, smart phone, tablet computer, desktop computer, laptop, mobile computing device, mobile phone, personal digital assistant (PDA), hybrid PDA/mobile phone, any electronic device configured to communicate over a network, or any device configured for the internet of things.

The health care module can be configured to obtain or generate heath data from a user of the wireless communicates device. For example, the health care module can include one or more sensors configured to obtain physiological data. In some cases, the mobile device 100 includes an emitter and a detector for obtaining one or more physiological measurements. In some cases, the health data is private, sensitive, confidential and/or HIPPA protected.

The mobile device can include one or more processors. The one or more processors can be configured to implement a third party application, such as a mobile app. In some cases, the user can adjust privacy-related settings (for example, permissions) for third party applications. For example, in some cases, the user can choose to prevent the third party application from obtaining, or having access to, private or sensitive data, such as health data. Alternatively, in some cases, the user can choose to allow the third party application to obtain, or have access to, private or sensitive data. In some cases, the mobile communications device includes a dedicated privacy switch that is implemented in hardware or software. In some cases, activation of the dedicated privacy switch can cause the mobile device to prevent the third party application from obtaining the private or sensitive data. For example, for data that is generated while the privacy switch is activated, the third party application may not have access to such data while the privacy switch is activated and/or after the privacy switch is deactivated. In some implementations, deactivation of the dedicated privacy switch can cause the mobile device to allow the third party application to obtain or access the private or sensitive data. In some cases, activation of the dedicated privacy switch can cause the mobile device to temporarily prevent the third party application from obtaining the private or sensitive data for a first period of time (for example, 30 minutes, 1 hour, 8 hours, 24 hours, 1 week, etc.). In some cases, the third party application is automatically allowed to resume obtaining the private or sensitive data after the expiration of the first period of time. Furthermore, in some cases, deactivation of the dedicated privacy switch can cause the mobile device to temporarily allow the third party application to obtain the private or sensitive data for a second period of time. In some cases, the third party application is automatically prevented from obtaining the private or sensitive data after the expiration of the second period of time.

The mobile device can identify some or all of the private or sensitive data, including data obtained or generated by the health care module. For example, the mobile device can associate an attribute (for example, use metadata to tag) with all of the private or sensitive data obtained or generated by the health module. In some such cases, in response to the activation of the dedicated privacy switch and for the duration of the first period of time, the mobile device can prevent transmission of or access to any data associated with the attribute. In some cases, the private or sensitive data is restricted by default. A user can give permission sell the private or sensitive data to the third party application. In some cases, the user shares in income from the sale of the private or sensitive data.

Figure 6A:
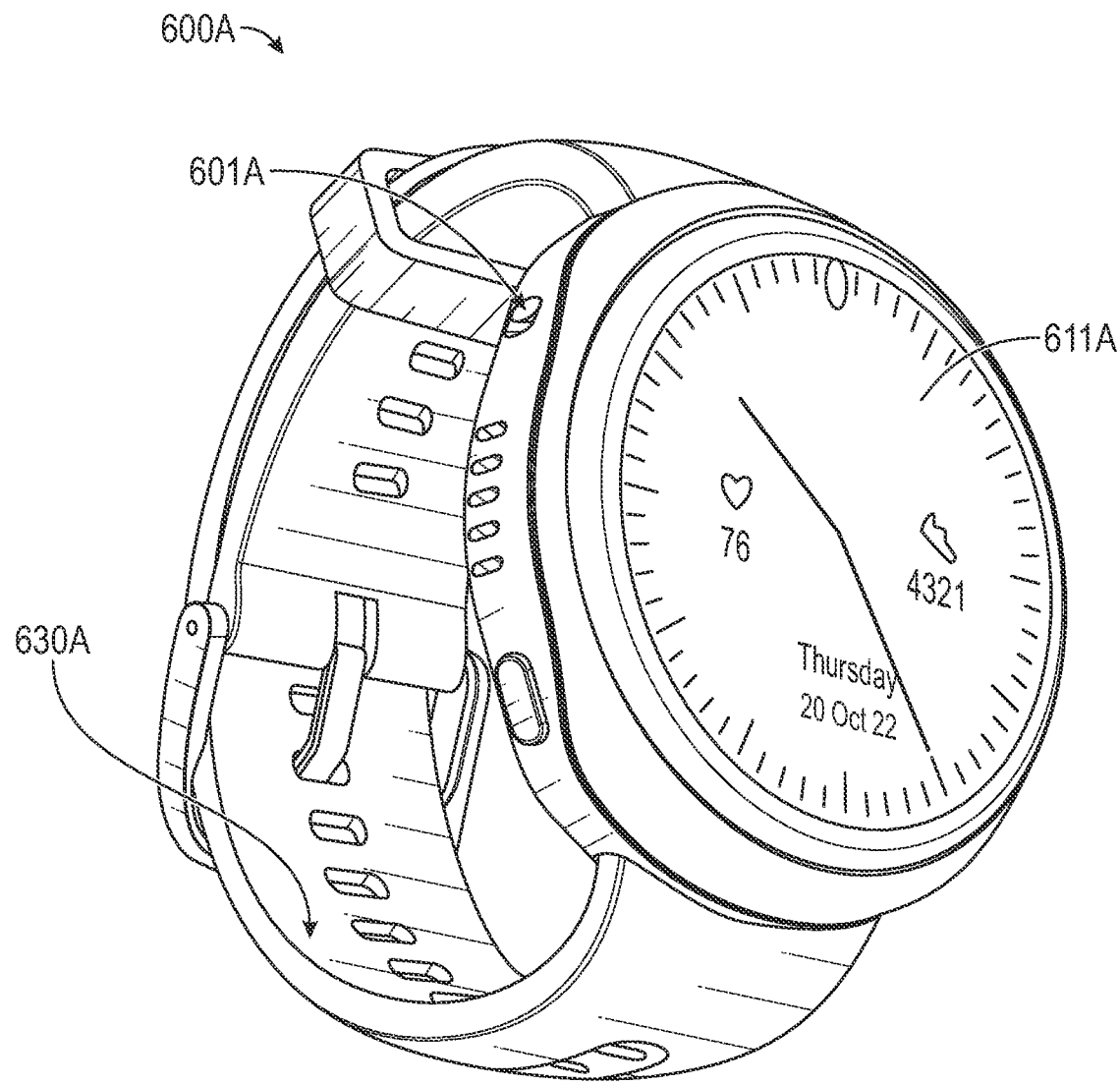
FIGS. 6A-6B are perspective views of example mobile devices.

FIG. 6A is a perspective view of an example mobile device 600A. The mobile device 600A may be a wearable device such as a smartwatch. FIG. 6A is not intended to be limiting of the present disclosure. One or more of any of the structural and/or operational features shown and/or discussed with respect to mobile device 600A, or any of the other mobile devices herein, may be implemented in any of the example computing devices discussed herein such as a phone, a laptop, a computer, a tablet, or any other computing device, for example.

The mobile device 600A may include a display 611A. The display 611A may be an LED display. The display 611A may be configured to display day, month, date, year, and/or time. The display 611A may display time as analog or digital. The display 611A may display physiological related data such as physiological parameters, physiological trends, physiological graphs, or the like. For example, the display 611A may display heart rate, respiration rate, ECG data, SpO2, a step count of the number of steps taken by a user of the mobile device 600A, or the like.

The mobile device 600A may include one or more straps 630A. The straps 630A may be adjustable. The straps 630A may be configured to secure the mobile device 600A to a body part of a user of the mobile device 600A, such as a wrist.

The mobile device 600A may include an actuator 601A. The actuator 601A may include one or more physical components. For example, the actuator 601A may be a switch, a lever, a button, a dial, a knob, a rocker, a toggle, or the like. The actuator 601A may be a slideable switch. The actuator 601A may include one or more electrical components. For example, the actuator 601A may be a capacitive touch screen. In some implementations, the actuator 601A may be a button displayed on a touch screen, a slider displayed on a touch screen, or the like.

In some implementations, the actuator 601A may include a camera configured to capture images and a hardware processor configured to perform one or more image processing techniques such as facial recognition. In some implementations, the actuator 601A may include a microphone configured to capture audio input and a hardware processor configured to perform one or more audio processing techniques such as voice recognition.

The actuator 601A may transition between states such as a first state and second state. In some implementations, the states represent a physical state (for example, switch is in one position or another position). In some implementations, the states represent an electrical state (for example, change in electrical capacitance, resistance, or the like). The actuator 601A may be configured to actuate (for example, transition between states) in response to a physical input, such as a motion to slide a switch, depress a button, or the like. The actuator 601A may be configured to actuate (for example, transition between states) in response to an electrical input, such as a change in capacitance, voice recognition, facial recognition, or the like.

The actuator 601A may be located on a housing of the mobile device 600A. The actuator 601A may be adjacent to the display 611A. In some implementations, the actuator 601A may be included on the display 611A, such as a portion of the display 611A, for example, in implementations where the actuator 601A is a capacitive touchscreen.

A user may actuate the actuator 601A to cause the mobile device 600A to transition between a privacy mode and non-privacy mode. For example, the actuator 601A, when in a first state, may cause the mobile device 600A to enter a privacy mode, and the actuator 601A, when in a second state, may cause the mobile device 600A to enter a non-privacy mode. The mobile device 600A, or components thereof, may operate differently when in the privacy mode than when in the non-privacy mode. For example, one or more components of the mobile device 600A, such as a communication device, may not operate during a privacy mode. As another example, a hardware processor of the mobile device 600A may handle data, such as sensor data, differently during a privacy mode than during a non-privacy mode. The mobile device 600A may operate normally during a non-privacy mode.

In some implementations, the actuator 601A may cause the mobile device 600A to only transition between the privacy mode and non-privacy mode. For example, the actuator 601A may be dedicated to transitioning the mobile device 600A between privacy and non-privacy modes and may not serve any other purpose. Advantageously, an actuator 601A dedicated to only causing the mobile device 600A to transition between privacy and non-privacy states may provide an improved user experience for transitioning the mobile device between privacy and non-privacy modes by providing a simple and easy-to-understand process that does not involve determining which operations actuating the actuator 601A will affect, such as in implementations where the actuator 601A may affect other operations of the mobile device in addition to transitioning between privacy and non-privacy modes. In some implementations, the actuator 601A may cause to mobile device 600A perform other operations in addition to transitioning between privacy and non-privacy modes. For example, in some implementations, actuating the actuator 601A may also cause the mobile device to power on/off, may turn the display 611A on/off, or the like.

In some implementations, the actuator 601A may be a single component. In some implementations, the actuator 601A may be the only component necessary to transition the mobile device 600A between privacy and non-privacy modes. For example, a user may not need to perform any other operation, other than actuating the actuator 601A, to transition the mobile device 600A between privacy and non-privacy modes. Advantageously, the ability to transition the mobile device 600A between privacy and non-privacy states by only actuating the actuator 601A may provide an improved user experience for transitioning the mobile device between privacy and non-privacy modes by providing a simple and easy-to-understand process that does not involve multiple operations. For example, the privacy switch does not require actuating multiple actuators simultaneously or sequentially. In some implementations, more than one operation may be required to transition the mobile device 600A between privacy and non-privacy modes. This can include actuating more than one actuator.

Advantageoulsy, a user may be able to easily toggle the mobile device 600A between privacy modes and non-privacy modes by actuating the actuator 601A.

Figure 6B:
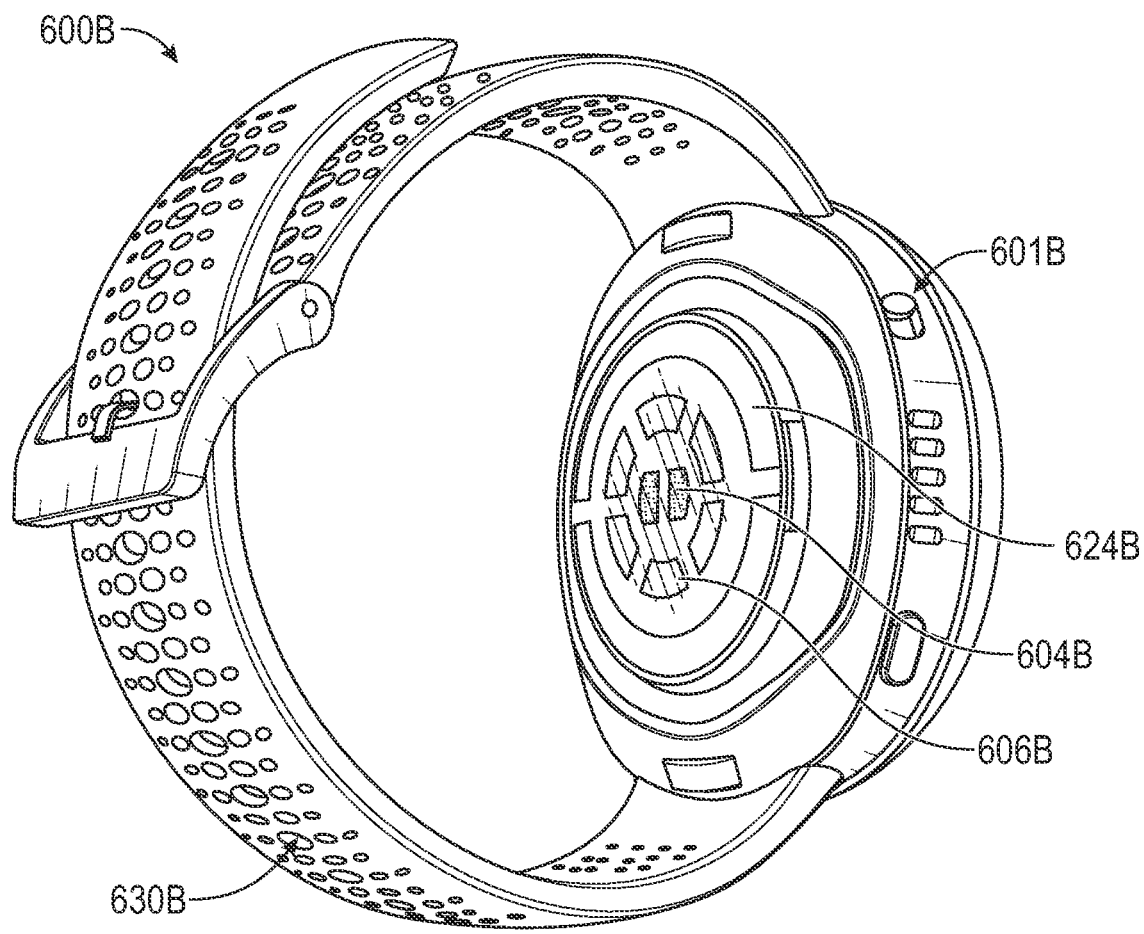

FIG. 6B is a perspective view of an example mobile device 600B. The mobile device 600B may include any of the same or similar operational and/or structural features shown and/or discussed with respect to the mobile device 600A of FIG. 6A. The mobile device 600B can include one or more straps 630B. The mobile device 600B can include an actuator 601B. The actuator 601B may include any of the same or similar operational and/or structural features shown and/or discussed with respect to the actuator 601A of FIG. 6A. The mobile device 600B can include one or more sensors such as physiological sensors.

The mobile device 600B can include one or more electrodes 624B. The electrode(s) 624B can be configured to contact the skin of a user of the mobile device 600B. The electrodes 624B can be configured to measure electrical activity. The electrode(s) 624B may obtain data related to the cardiac activity of a user of the mobile device 600B, such as ECG data.

The mobile device 600B can include one or more emitters 604B. The emitter(s) 604B can include one or more light emitting diodes (LEDs). The emitter(s) 604B may emit light of various wavelengths which may penetrate into a tissue of the user of the mobile device 600B.

The mobile device 600B can include one or more detectors 606B. The detector(s) 606B may detect light emitted by the emitter(s) 604B. The detector(s) 606B may generate one or more signals based at least in part on the light detected that was emitted by the emitter(s) 604B. The detector(s) 604B may generate data relating to blood oxygen saturation of a user of the mobile device 600B. The detector(s) 604B may generate data relating to spectroscopy.

The actuator 601B may be located on a housing of the mobile device 600B. The sensor(s) of the mobile device 600B, such as the electrode(s) 624B, the emitter(s) 604B, and/or the detector(s) 606B, may be located on a housing of the mobile device 600B. The actuator 601B may be located on a different portion of the mobile device 600B housing than one or more of the sensors. The actuator 601B may not be in physical contact with one or more of the sensors of the mobile device 600B. In some implementations, the actuator 601B may be located on a portion of the mobile device 600B housing that is accessible to a user to actuate the actuator 601B. In some implementations, one or more of the sensors of the mobile device 600B may be located on a portion of the mobile device 600B housing that is not readily accessible to user. For example, a user may not be able to access the one or more sensors with their fingers. For example, the sensors may be located on an underside portion of the mobile device 600B such that when the mobile device 600B is worn by a user, the mobile device 600B covers the sensors against the user, such as against a wrist area of the user such that the user may not be able to readily access the sensors with their fingers. Advantageously, a user may be able to easily actuate the actuator 601B without interfering with or disrupting the sensors, such as data collection of the sensors, because the actuator 601B and sensors are located on different portions of the mobile device 600B housing, for example. For example, the sensors may continue to operate when a user actuates the actuator 601B between states. In some implementations, the actuator 601B may not cover or block one or more of the sensors when the actuator is in any of the actuator states.

In some implementations, the actuator 601B may be located on a same portion of mobile device 600B housing as some sensors and a different portion of the mobile device 600B housing than other sensors. In some implementations, some sensors may be located on a different portion of the mobile device 600B housing than other sensors.

Figure 7:
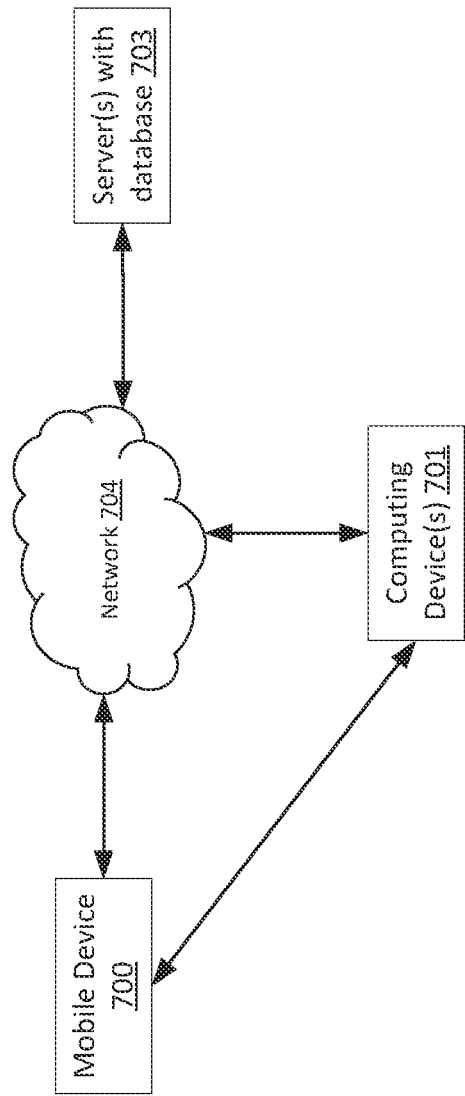
FIG. 7 is a schematic block diagram illustrating an example implementation of a mobile device in communication with one or more remote devices.

FIG. 7 is a schematic block diagram illustrating an example implementation of a mobile device 700 in communication with one or more devices remote to the mobile device 700. Mobile device 700 can communicate with one or more servers 703 via a network 704. The network 704 can include any combination of networks, such as a personal area network (PAN), a local area network (LAN), a metropolitan area network (MAN), a wide area network (WAN), or the like. The mobile device 700 may, via the network 704, communicate data to the server(s) 703 and/or receive data from the servers(s) 703, such as sensor data which may include physiological data.

The server(s) 703 may include, be in communication with, and/or have access to a database or storage device or system which can include any computer readable storage medium and/or device (or collection of data storage mediums and/or devices), including, but not limited to, one or more memory devices that store data, including without limitation, dynamic and/or static random access memory (RAM), programmable read-only memory (PROM), erasable programmable read-only memory (EPROM), electrically erasable programmable read-only memory (EEPROM), optical disks (e.g., CD-ROM, DVD-ROM, etc.), magnetic disks (e.g., hard disks, floppy disks, etc.), memory circuits (e.g., solid state drives, random-access memory (RAM), etc.), and/or the like. In some implementations, the server(s) 703 may include and/or be in communication with a hosted storage environment that includes a collection of physical data storage devices that may be remotely accessible and may be rapidly provisioned as needed (commonly referred to as "cloud" storage). Data stored in and/or accessible by the server(s) 703 can include sensor data, such as physiological data, including historical physiological data previously obtained by one or more sensors of the mobile device 700.

Mobile device 700 can communicate with one or more computing devices 701 via the network 704. The computing device(s) 701 may include one or more of a laptop, a tablet, a phone, a smart device, a smart watch, a patient monitoring device or hub, a home monitoring system, or the like. In some implementations, the computing device(s) 701 may include a same or similar device as the mobile device 700. The mobile device 700 may, via the network 704, communicate data to the computing device(s) 701 and/or receive data from the computing device(s) 701, such as sensor data which may include physiological data. In some implementations, the mobile device 700 may communicate with the computing device(s) 701 directly such as via a wireless and/or wired communication protocol.

The mobile device 700 may communicate directly with the computing device(s) 701 and/or server(s) 703 via a wireless communication protocol including one or more of WiFi, Bluetooth, near field communication (NFC), radio frequency identification (RFID), cellular, 1G, 2G, 3G, 4G, 5G, Zigbee, Z-wave, and/or the like.

In some implementations, the mobile device 700 may communicate with the server(s) and/or computing devices 701 during a non-privacy mode. In some implementations, the mobile device 700 may not communicate with the server(s) and/or computing devices 701 during a privacy mode. For example, the mobile device 700 may not be capable of communicating with the server(s) and/or computing devices 701 during a privacy mode because a communication device of the mobile device 700 may be powered off.

Figure 8A:
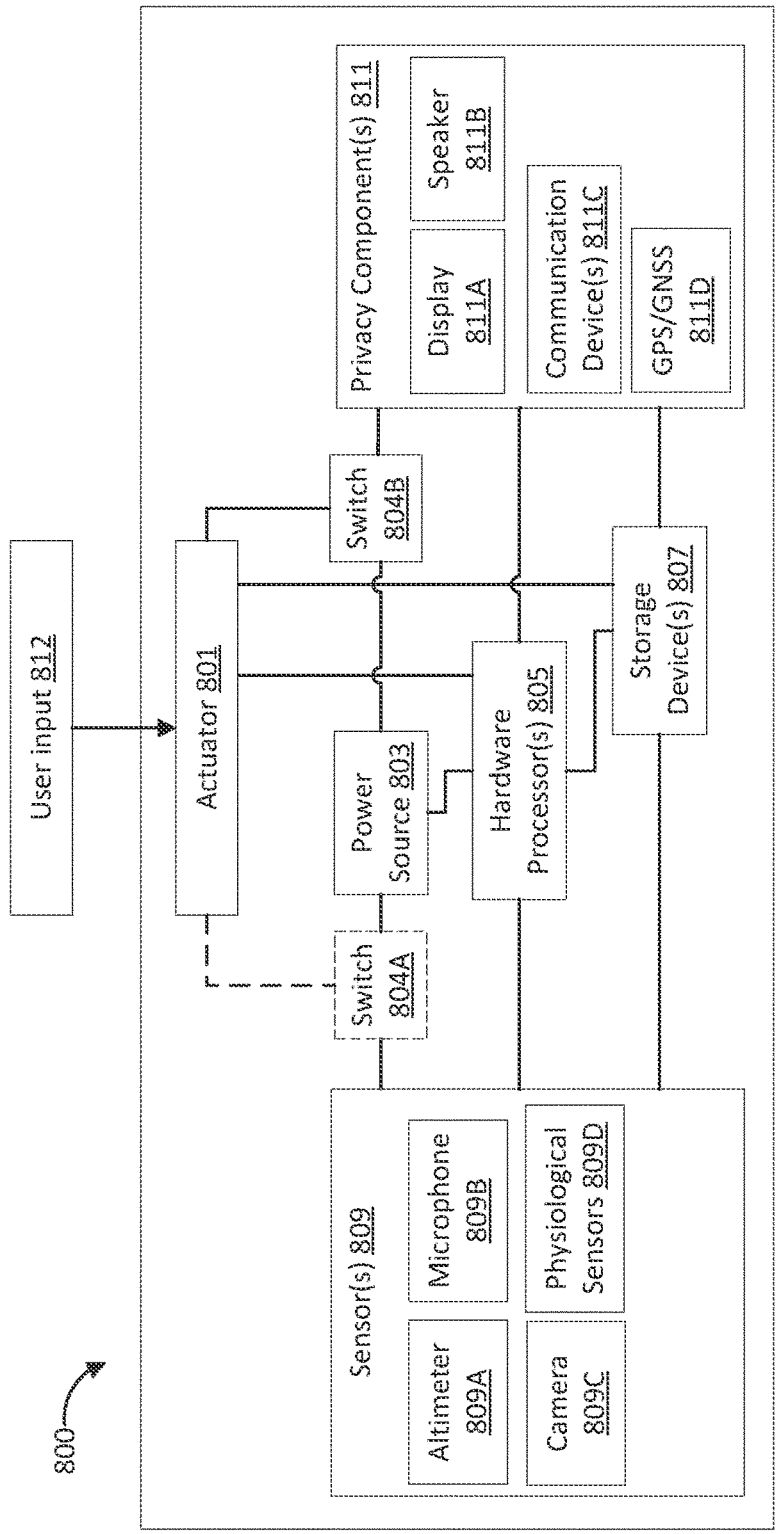
FIG. 8A is a schematic block diagram illustrating an example implementation of a mobile device.

FIG. 8A is a schematic block diagram illustrating an example implementation of a mobile device 800. The mobile device 800 can include an actuator 801, one or more sensors 809, one or more privacy components 811, a power source 803, one or more hardware processors 805, one or more storage devices 807, and one or more switches such as switch 804A and/or switch 804B. In some implementations, the mobile device 800 may not include switch 804A.

The power source 803 can provide power to hardware components of the mobile device 800 described herein. The power source 803 can include a battery. The power source 803 can be, for example, a lithium battery. Additionally or alternatively, the mobile device 800 can be configured to obtain power from a power source that is external to the mobile device 800. For example, the mobile device 800 can include or can be configured to connect to a cable which can itself connect to an external power source to provide power to the mobile device 800.

The switch(es) 804 (such as switch 804B and/or switch 804A) can include an electrical switch, relay, conductor, circuit breaker, or the like. The switch(es) 804 can include a two-way, three-way, four-way switch, or the like. The switch(es) 804 can include a single pole, single throw (SPST) switch, a single pole, double throw (SPDT) switch, a double pole, single throw (DPST) switch, a double pole, double throw (DPDT) switch, or the like. The switch(es) 804 can be configured to transition between one or more states, such as in response to input from the actuator 801. In some implementations, the switch(es) 804 may transition between one or more states in response to a signal from the processor(s) 805. In some implementations, the switch(es) 804 may transition between states automatically based, at least in part, on one or more conditions such as time, location of the wearable device 800, or the like. The switch(es) 804 can be configured to conduct energy in a first state and not conduct energy in a second state. The switch 804B can be configured to electrically disconnect the privacy component(s) 811 from the power source 803. The switch 804A can be configured to electrically disconnect the sensor(s) 809 from the power source 803. In some implementations, the switch 804A may be different than switch 804B. In some implementations, switch 804A may be the same as switch 804B.

The processor(s) 805 can be configured, among other things, to process data, execute instructions to perform one or more functions, and/or control the operation of the mobile device 800, or components thereof. For example, the processor(s) 805 can process data obtained from the sensor(s) 809 and can execute instructions to perform functions related to processing, storing, displaying, and/or transmitting such data.

The storage device(s) 807 can include one or more memory devices that store data, including without limitation, dynamic and/or static random-access memory (RAM), programmable read-only memory (PROM), erasable programmable read-only memory (EPROM), electrically erasable programmable read-only memory (EEPROM), and the like. Such stored data can be data obtained from the sensor(s) 809 which can include processed and/or unprocessed physiological data, for example.

The sensor(s) 809 can include an altimeter 809A, a microphone 809B, a camera 809C, and/or one or more physiological sensors 809D. FIG. 8A is not intended to be limiting of the present disclosure. In some implementations, the sensor(s) 809 may include additional sensors not shown. In some implementations, the sensor(s) 809 may include fewer sensors than what are shown.

The sensor(s) 809 can generate sensor data, for example in response to obtaining, measuring, and/or collecting input data. The altimeter 809A can generate altitude data in response to obtaining barometric pressure data. The microphone 809B can generate audio data in response to receiving audio input. The camera 809B can generate image and/or video data in response to capturing image input. The physiological sensor(s) can generate physiological data in response to obtaining physiological measurements of user of the mobile device 800. The physiological sensor(s) 809D can include one or more of electrodes, emitters, detectors, thermistor, gyroscope, accelerometer, or the like.

The privacy component(s) 811 can include a display 811A, a speaker 811B, one or more communication devices 811C, and/or a GPS/GNSS device 811D. FIG. 8A is not intended to be limiting of the present disclosure. In some implementations, the privacy component(s) 811 may include additional devices not shown. In some implementations, the privacy component(s) 811 may include fewer devices than what are shown. In some implementations, the privacy component(s) 811 may not include a display 811A and/or a speaker 811B.

The display 811A may display one or more images relating to sensor data. For example, the display 811A may display physiological parameters or data obtained from one or more physiological sensors 809D. The display 811A may include an LED display.

The speaker 811B may output auditory signals. The auditory signals can include an alarm. The auditory signals may relate to sensor data such as data from physiological sensors 809D. The auditory signals can include sounds and/or verbal words.

The GPS/GNSS 811D may facilitate communication between the mobile device 800 (and/or components thereof) and separate devices such as one or more satellites. The GPS/GNSS may transmit and/or receive data relating to a geographic location of the GPS/GNSS 811D and mobile device 800. The GPS/GNSS 811D can include a transceiver, an antenna, or the like. In some implementations, the GPS/GNSS 811D may be embodied in the communication device 811C.

The communication device(s) 811C can facilitate communication (via wired and/or wireless connection) between the mobile device 800 (and/or components thereof) and separate devices, such as separate computing devices, sensors, systems, servers, or the like. For example, the communication device(s) 811C can be configured to allow the mobile device 800 to wirelessly communicate with other devices, systems, and/or networks over any of a variety of communication protocols. The communication device(s) 811C can be configured to use any of a variety of wireless communication protocols, such as Wi-Fi (802.11x), Bluetooth®, ZigBee®, Z-wave®, cellular telephony, infrared, near-field communications (NFC), radio frequency identification (RFID), 1G, 2G, 3G, 4G, 5G, satellite transmission, proprietary protocols, combinations of the same, and/or the like. The communication device(s) 811C can allow data and/or instructions to be transmitted and/or received to and/or from the mobile device 800 and separate computing devices. The communication device(s) 811C can be configured to transmit and/or receive (for example, wirelessly) sensor data such as processed and/or unprocessed physiological data with separate computing devices remote to the mobile device 800, remote servers, or the like. The communication device(s) 811C can be embodied in one or more components that are in communication with each other. The communication device(s) 811C can include a wireless transceiver, an antenna, and/or a near field communication (NFC) component such as a transponder.

The power source 803 may be in electrical communication with the privacy component(s) 811 via switch 804B. The power source 803 may be removably electrically coupled with the privacy component(s) 811 via the switch 804B. For example, the switch 804B may electrically connect the power source 803 with the privacy component(s) 811 in a first state and may electrically disconnect the power source 803 from the privacy component(s) 811 in a second state. The switch 804B may transition between states in response to actuation of the actuator 801.

Transitioning of the switch 804B between states may correspond to various modes of operation of the mobile device 800. For example, the switch 804B may electrically disconnect the power source 803 from the privacy component(s) 811 during a privacy mode operation and may electrically connect the power source 803 to the privacy component(s) 811 during a non-privacy mode operation. One or more of the privacy component(s) 811 may not operate when disconnected from the power source 803 by the switch 804B, such as during a privacy mode. Advantageoulsy, when the privacy component(s) 811 are electrically disconnected from the power source 803 by the switch 804B, such as during a privacy mode, the mobile device may protect sensitive data, such as sensitive sensor data, by preventing the data from being transmitted, obtained, received, viewed, heard, or the like, by other computing devices, people, etc., for example. For example, during a privacy mode, when the privacy component(s) 811 may be electrically disconnected from the power source 803, the communication device(s) 811C may not be capable of communicating data to one or more remote devices at least because the communication device(s) 811C are powered off. As another example, during a privacy mode, the communication device(s) 811C may not be capable of receiving data, such as phone calls, text messages, email messages, software updates, notifications, or the like, from one or more remote devices at least because the communication device(s) 811C are powered off. As another example, during a privacy mode, display 811A may be disabled. For example, the display 811A may not display data, such as physiological data, at least because the display 811A is powered off, which may prevent certain people from viewing the data on the display 811A such as when a user of the mobile device 800A is in a public area and does not desire other people to view data displayed via the display 811A. As another example, during a privacy mode, the speaker 811B may not be capable of outputting an audio signal, at least because the speaker 811B is powered off, which may prevent certain people from hearing audio signals relating to sensitive data such as when a user of the mobile device 800 is in a public area and does not desire other people to hear audio sounds relating to certain data, such as voice audio reciting physiological parameters of the user. As another example, during a privacy mode, the GPS/GNSS 811D may not be capable of determining a location of the GPS/GNSS 811D and/or the mobile device 800, at least because the GPS/GNSS 811D is powered off, which may prevent other computing devices and/or people from receiving, obtaining data relating to the location of the GPS/GNSS 811D and/or the mobile device 800.

In some implementations, the switch 804B may transition between states to electrically connect/disconnect each of the privacy component(s) 811 collectively from the power source 803. For example, the switch 804B may electrically connect/disconnect the power source 803 with each of the privacy component(s) 811 via a single pole. In some implementations, the switch 804B may transition between states to electrically connect/disconnect the privacy component(s) 811 from the power source 803 independently of one another. For example, the switch 804B may electrically connect/disconnect some or all of the privacy component(s) 811 with the power source 803 individually such as via multiple switches or multiples poles. For example, each pole may correspond to a unique device of the privacy component(s) 811.

As an example, the switch 804B may electrically connect each of the privacy component(s) 811 with the power source 803 in a first state and may electrically disconnect each of the privacy component(s) 811 from the power source 803 in a second state. As another example, the switch 804B may electrically connect a first group of privacy component(s) 811 with the power source 803 in a first state and may electrically connect a second group of privacy component(s) 811 with the power source 803 in a second state and may electrically connect each of the privacy component(s) 811 with the power source 803 in a third state and may electrically disconnect each of the privacy component(s) 811 from the power source 803 in a fourth state.

In some implementations, the power source 803 may be in electrical communication with the privacy component(s) 811 optionally via switch 804B. The power source 803 may be removably electrically coupled with the privacy component(s) 811 via the switch 804B. For example, the switch 804B may electrically connect the power source 803 with the privacy component(s) 811 in a first state and may electrically disconnect the power source 803 from the privacy component(s) 811 in a second state. The switch 804B may transition between states in response to actuation of the actuator 801. The switch 804A may include similar and/or the same structural and/or operational features discussed with respect to switch 804B.

In some implementations, the power source 803 may be in direct electrical communication with the privacy component(s) 811. For example, the power source 803 may not be electrically coupled with the privacy component(s) 811 via the switch 804A. For example, the sensor(s) 809 may be in electrical communication with the power source 803 and may receive power therefrom whether during a privacy mode or non-privacy mode. Advantageoulsy, the sensor(s) 809 may continue to operate during a privacy mode of the mobile device 800. In some implementations, the sensor(s) 809 may continue to operate regardless of actuation of the actuator 801. Advantageoulsy, the sensor may continue to generate sensor data whether during a privacy mode or non-privacy mode such that the sensor data may be continuous over a length and/or may not include any gaps due to changes in modes of operation. Advantageously, a continuous set of data may be important and may improve data monitoring and/or analysis, such as when analyzing trends in data, as is often the case with physiological data, for example, for which a user may desire to have access to an uninterrupted series of data. Advantageously, the mobile device 800 may still protect sensitive sensor data that is generated during a privacy mode such as by preventing the sensor data from being communicated to any external devices, for example, at least because the communication device 811C is powered off during a privacy mode. Advantageously, a user of the mobile device 800 may still have access to all sensor data, including sensitive sensor data, generated during a privacy mode. For example, the sensor(s) 809 may generate sensor data during a privacy mode and the display 811A may display that sensor data during and/or after the privacy mode such that a user of the mobile device 800 may view the sensitive sensor data. However, the mobile device 800 may still protect such sensitive sensor data by preventing the communication device 811C from communicating the sensor data to remote devices during and/or after the privacy mode, for example. Accordingly, the mobile device 800 may continue to generate sensor data during a privacy mode while still protecting that sensor data.

The mobile device 800 may receive a user input 812, such as via the actuator 801. The user input 812 can include a physical motion or movement such as a mechanical force to push, slide, switch, toggle, move, etc. the actuator 801. The user input 812 can include an electrical force or signal, such as a change in capacitance on a capacitive touchscreen, a change in voltage, a change in current, or the like. The user input 812 can include one or more auditory signals, such as a voice command detected by a microphone and processed by a processor (for example, using voice recognition), to actuate the actuator 801. The user input 812 can include one or more visual signals, such as an image of a face captured by a camera and processed by a processor (for example, using face recognition), to actuate the actuator 801.

The actuator 801 may change states based on the user input 812. Actuation of the actuator 801 may cause the switch 804A and/or the switch 804B to change states, which may cause the mobile device 800 to transition between one or more operating modes, such as privacy and non-privacy modes. The actuator 801 may be directly physically and/or electrically connected with the switch 804A and/or the switch 804B. For example, the actuator 801 may be hardwired with the switch 804A and/or the switch 804B. Advantageoulsy, a direct connection between the actuator 801 and the switch(es) 804 may ensure that actuation of the actuator 801 causes the switch(es) 804 to change state. Advantageoulsy, transitioning the switch(es) 804 between states may depend only on actuating the actuator 801 (which may be a physical action), and may not depend on program instructions, such as instructions generated by a hardware processor, which may reduce the risk of erroneous operation caused by software bugs, software hacking, software incompatibilities, or the like.

The actuator 801 is in communication with the processor(s) 805. The actuator 801, or actuation thereof, may cause the processor(s) 805 to perform one or more operations and/or change mode of operation. For example, the processor(s) 805 may process data differently based on actuation of the actuator 801.

The processor(s) 805 may receive sensor data from the sensor(s) 809. The processor(s) 805 may tag sensor data with metadata. The metadata can include identifiers to specify one or more attributes of the sensor data, such as a time the sensor data was generated, a mode of operation (for example, privacy, non-privacy) during which the sensor data was generated, a location the sensor data was generated, a sensitivity level of the sensor data, or the like. The 805 may assign and/or update the metadata of the sensor data based at least on actuation of the actuator 801. Advantageously, metadata of the sensor data can improve efficiency with which the data is handled and improve protection of sensitive data. For example, the processor(s) 805 may perform one or more operations relating to the sensor data according to metadata of the sensor data. The processor(s) 805 may handle certain sensor data, such as sensitive data, differently based on its metadata. The processor(s) 805 may be able to quickly and efficiently identify data that should be handled differently based on the metadata, which may lead to faster search times when accessing and/or retrieving data such as from storage.

The 43econd43sor(s) 805 may store sensor data in the storage device(s) 807. In some implementations, the processor(s) 805 may store all sensor data received from the sensor(s) 809. For example, the processor(s) 805 may store sensor data regardless of whether the sensor data was received from and/or generated by the sensor(s) 809 during a privacy mode. In some implementations, the processor(s) 805 may not delete sensor data received from and/or generated by the sensor(s) 809 during a privacy mode. Advantageously, sensor data, whether received and/or generated during a privacy mode, may be stored in the storage device(s) 807 and thus the mobile device 800 may have access to all of the sensor data, while still protecting sensitive data as described herein. This may reduce the amount data that is lost and/or deleted for being sensitive but which may still be valuable and desirable to be kept, although being sensitive and requiring protection. In some implementations, the processor(s) 805 may delete and/or may not save to storage sensor data received from and/or generated by the sensor(s) 809 during a privacy mode.

The processor(s) 805 may store all of the sensor data in a same storage device and/or similar location in storage. For example, the storage device(s) 807 may include a single storage device configured to store all of the sensor data. In some implementations, the processor(s) 805 may store all of the sensor data in a similar manner and/or location, such as regardless of whether the sensor data was received and/or generated during a privacy mode, for example. Advantageously, the processor(s) 805 may identify, retrieve, and/or access sensor data from storage based on metadata of the sensor data, and not based on sensor data location in storage. Advantageously, by identifying its metadata, the processor(s) 805 may be able to more quickly access the sensor data, at least because the processor(s) 805 will not have to search across multiple storage locations and/or devices. Advantageously, the processor(s) 805 may not be required to expend time and processing power to allocate storage, partition storage, segregate storage, etc. to store sensitive data differently than other data. Advantageously, the entire storage device(s) 807 may be available to store any data (for example, sensitive or non-sensitive) which may improve memory requirements, such as by reducing the need to allocate a relatively large amount of storage space for a relatively small amount of data such as sensitive data. Advantageously, eliminating the need to allocate particular storage for certain data, such as sensitive data, may reduce the amount of storage space required by the mobile device 800.

Advantageously, the processor(s) 805 and/or storage device(s) 807 may be in direct communication with the sensor(s) 809. For example, the storage device(s) 807 and/or storage device(s) 807 may be in communication with the sensor(s) 809 regardless of whether the mobile device 800 is in a privacy mode or non-privacy mode and/or whether the actuator 801 is actuated.

Figure 8B:
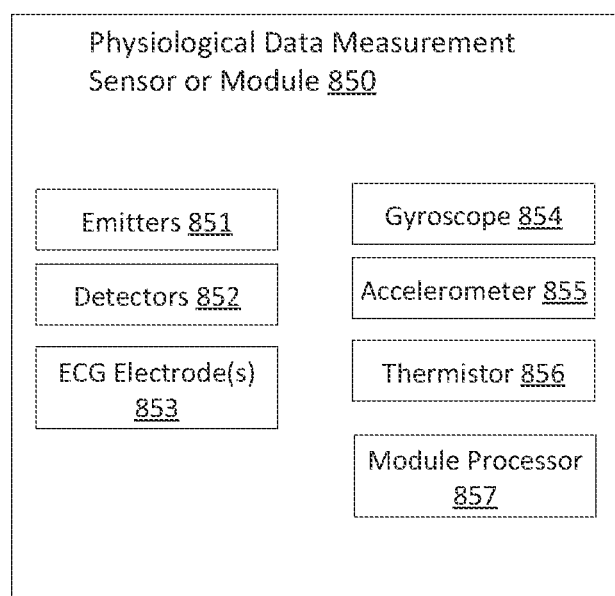
FIG. 8B is a block diagram of an example physiological data measurement sensor or module of a mobile device.

FIG. 8B is a block diagram of an example physiological data measurement sensor or module 850 which may be incorporated in a mobile device, such as any of the example mobile devices shown and/or discussed herein. For example, the physiological data measurement sensor or module 850 may be included as one or more of sensor(s) 809 shown and/or discussed with respect to FIG. 8A.

The sensor or module 850 can include a sensor or module processor 857 (which can include a memory and/or other electronics). The sensor or module processor 857 can process signals from one or more of the sensors in the sensor or module 850 (or optionally other sensors) to determine a plurality of physiological parameters. In some implementations, the sensor or module processor 857 may perform some or all of the processing of the raw sensor data of the sensors in communication (via a wired and/or wireless connection) with the sensor or module processor 857. The sensor or module processor 857 can be configured to drive the emitters 851 to emit light of different wavelengths and/or to process signals of attenuated light after absorption by the body tissue of the user from the detectors 852. The sensor or module processor 857 can determine and output for display of the physiological parameters based on the detected signals. Optionally, the sensor or module 850 can send the signals from the detectors 852 another processor, which can determine and output for display the physiological parameters based on the detected signals. The absorption of light can be via transreflectance by the user's body tissue, for example, by the pulsatile arterial blood flowing through the capillaries (and optionally also the arteries) within a tissue site where the sensor or module 850 is worn (for example, the wrist).

The physiological data measurement sensor or module 850 is configured to measure an indication of the user's physiological parameters. This can include, for example, pulse rate, respiration rate, $SpO_2$, Pleth Variability Index (PVI), Perfusion Index (PI), Respiration from the pleth (RRp), total hemoglobin (SpHb), hydration, glucose, blood pressure, hydration index, and/or other parameters. The sensor or module 850 can perform intermittent and/or continuous monitoring of the measured parameters. The sensor or module 850 can additionally and/or alternatively perform a spot check of the measured parameters, for example, upon request by the user.

The sensor or module 850 can include more than one group or cluster of light emitters (such as LEDs) 851 and more than one group of photodetectors (also referred to as "detectors") 852. Each group of emitters 851 can be configured to emit four (or more) different wavelengths described herein.

The emitters 851 of the sensor or module 850 can be configured to emit a plurality of (for example, three, four, or more) wavelengths. The emitters 851 can be configured to emit light of a first wavelength providing an intensity signal that can act as a reference signal. The first wavelength can be more absorbent by the human body than light of other wavelengths emitted by the emitters 851. The reference signal can be used by the module processor 857 to extract information from the other signals, for example, information relevant to and/or indicative of the pulsing rate, harmonics, or otherwise. The module processor 857 can focus the analysis on the extracted information for calculating the physiological parameters of the user. The first wavelength can include a range of wavelengths, including, for example, from about 530 nm to about 650 nm, or from about 580 nm to about 585 nm, or from about 645 nm to about 650 nm, or about 580 nm, or about 645 nm. The light providing the reference signal can have an orange color. Alternatively, the light providing the reference signal can have a green color.

The emitters 851 can be configured to emit light of a second wavelength having a red or orange color. The second wavelength can be from about 620 nm to about 660 nm. Light of the second wavelength can be more sensitive to changes in SpO2. The second wavelength is preferably closer to 620 nm, which results in greater absorption by the body tissue of the user, and therefore a stronger signal and/or a steeper curve in the signal, than a wavelength that is closer to 660 nm. The module processor 857 can extract information such as the pleth waveform from signals of the second wavelength. The emitters 851 can be configured to emit light of a third wavelength of about 900 nm to about 970 nm, or about 905 nm, or about 907 nm. The pulse oximeter processor can use the third wavelength as a normalizing wavelength when calculating ratios of the intensity signals of the other wavelengths.

Additionally or optionally, the emitters 851 can be configured to emit light having a fourth wavelength that is more sensitive to changes in water than the rest of the emitted wavelengths. The fourth wavelength can be about 970 nm or higher than 970 nm. The module processor 857 can determine physiological parameters such as a hydration status of the user based at least in part on a comparison of the intensity signals of the fourth wavelength and a different wavelength detected by certain detectors 852.

The sensor or module 850 can include a gyroscope 854, an accelerometer 855, and/or other position and/or posture detection sensor(s). The gyroscope 854 and/or the accelerometer 855 can be in electrical communication with the sensor or module processor 857. The module processor 857 can determine motion information from signals from the gyroscope 854 and/or the accelerometer 855. The motion information can provide noise reference for analysis of the pleth information and other signal processing (for example, processing of ECG signals) performed by the sensor or module processor 857.

The sensor or module 850 can include one or more thermistors 856 or other types of temperature sensors. The thermistor(s) 856 can be placed near one or more groups of emitters 851. There can be at least one thermistor 856 near each group of emitters 851. Optionally there can be one or more thermistors 856 located at other places of the sensor or module 850. The thermistor(s) 856 can provide for wavelength correction of the light emitted by the emitters 851. Optionally, the thermistor(s) 856 can measure a temperature of a user.

The sensor or module 850 can include an electrocardiogram (ECG) sensor including a plurality of electrodes 853 configured to make contact with the user's skin. One or more ECG electrodes 853 may be located on the sensor or module 850. One or more ECG electrodes may be located elsewhere on a mobile device. The ECG sensor can be in electrical communication with the module processor 857.

Figure 9A:
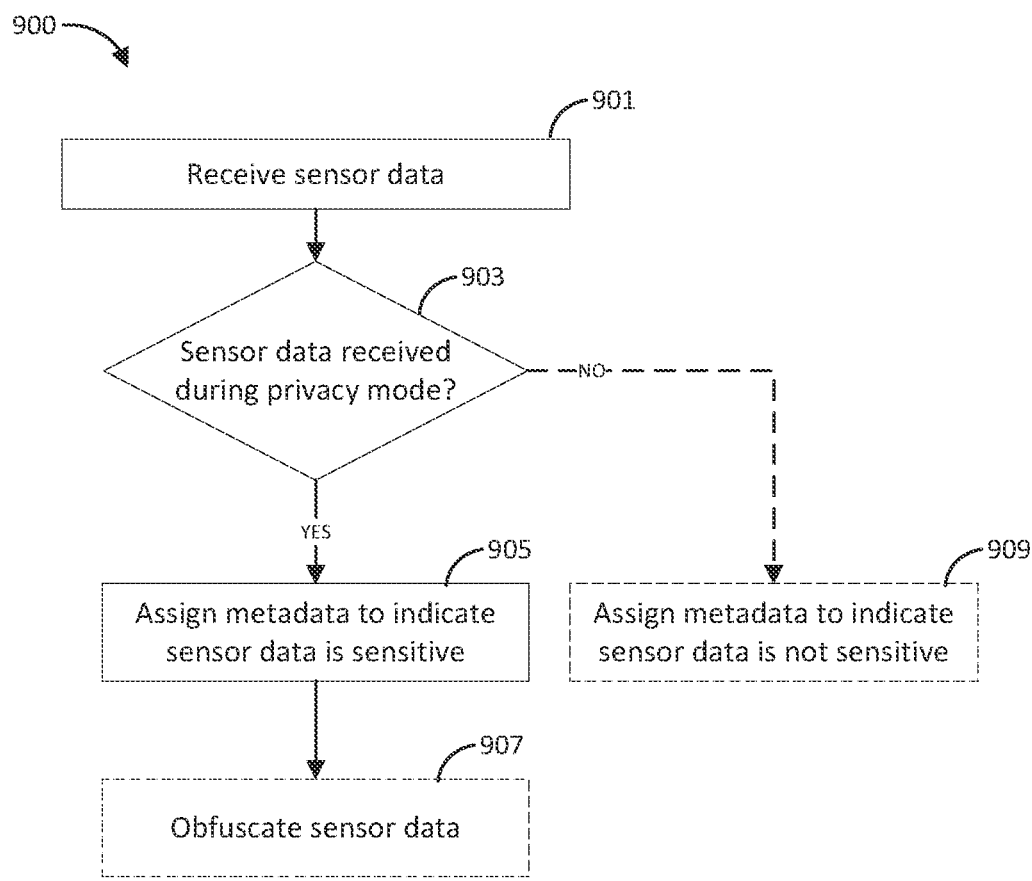
FIG. 9A is a flowchart illustrating an example process for assigning metadata of sensor data.

FIG. 9A is a flowchart illustrating an example process 900 for assigning and/or updating metadata of sensor data. The process 900, or portions thereof, can be implemented on a mobile device and executed by one or more hardware processors, such as hardware processor(s) 805 shown and/or described herein, at least with respect to FIG. 8A. Process 900 is provided as an example and is not intended to be limiting of the present disclosure. In some implementations, the processor may omit portions of the process 900, may add additional operations, and/or may rearrange an order of the operations shown. The processor can perform the process 900, or portions thereof, during a privacy mode and/or during a non-privacy mode.

At block 901, one or more hardware processors, such as hardware processor(s) 805, may receive sensor data. The sensor data can include data obtained, collected, and/or generated by one or more sensors, such as physiological sensors, microphones, altimeters, a camera, or the like. The sensor data can include physiological data. In some implementations, the processor may receive the sensor data at a same, or substantially same time as the sensor data is generated by the sensors.

At decision block 903, the processors can determine whether the sensor data was received during a privacy mode. In some implementations, the processor may determine whether the sensor data was generated by the sensors during a privacy mode. The processor may determine the occurrence of a privacy mode based, at least in part, on actuation of an actuator. If the processor determines that the sensor data was received during a privacy mode, the processor may proceed to block 905. If the processor determines that the sensor data was not received during a privacy mode, then the processor may proceed to block 909. For example, the processor may proceed to block 909 if the sensor data was received during a non-privacy mode.

At block 905, the processor may assign metadata of the sensor data to indicate the sensor data is sensitive. For example, the processor may create a tag, marker, or identifier to assign to the sensor data to indicate that the sensor data is sensitive. In some implementations, the processor may update existing metadata to indicate the sensor data is sensitive. Assigning metadata can include updating, changing, altering, tagging, creating, and/or deleting metadata. Advantageously, the processor may be able to quickly identify whether sensor data is sensitive or not, based on its metadata, and can handle the data accordingly.

At block 907, the processor can optionally obfuscate the sensor data. For example, the processor may encrypt the sensor data. In some implementations, the processor may encrypt the sensor data with a key that is stored locally on a mobile device of the processor. Advantageously, encrypting the sensor data may prevent the sensor data from being utilized, interpreted, useable, and/or decrypted by another computing device, for example, if the sensor data were communicated to another computing device.

At block 909, the processor may optionally assign the metadata of the sensor data to indicate the sensor data is not sensitive. For example, the processor may create a tag, marker, or identifier to assign to the sensor data to indicate that the sensor data is not sensitive. In some implementations, the processor may update existing metadata to indicate the sensor data is not sensitive. Assigning metadata can include updating, changing, altering, tagging, creating, and/or deleting metadata. In some implementations, the processor may not assign the metadata, which may also indicate the sensor data is not sensitive. Advantageously, the processor may be able to quickly identify whether sensor data is sensitive or not, based on its metadata, and can handle the data accordingly.

Figure 9B:
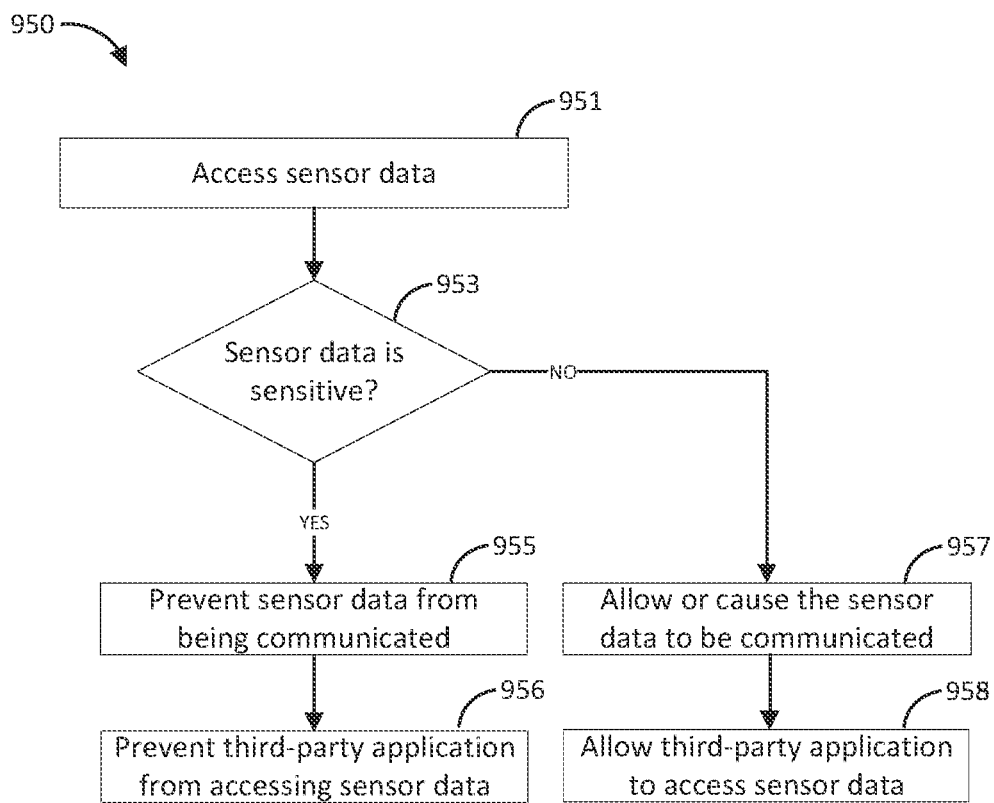
FIG. 9B is a flowchart illustrating an example process for determining whether to communicate sensor data.

FIG. 9B is a flowchart illustrating an example process 950 for determining whether to communicate sensor data. The process 950, or portions thereof, can be implemented on a mobile device and executed by one or more hardware processors, such as hardware processor(s) 805 shown and/or described herein, at least with respect to FIG. 8A. Process 950 is provided as an example and is not intended to be limiting of the present disclosure. In some implementations, the processor may omit portions of the process 950, may add additional operations, and/or may rearrange an order of the operations shown.

The processor can perform the process 950, or portions thereof, during a privacy mode and/or during a non-privacy mode. In some implementations, the processor may perform the process 950, or portions thereof, during a non-privacy mode when a communication device of a mobile device is powered on and/or operating.

At block 951, the processor can access sensor data. In some implementations, the processor can access sensor data stored in memory. In some implementations, the processor can access sensor data that is received in real-time from one or more sensors.

At decision block 953, the processor may determine whether the sensor data is sensitive. The processor may determine whether the sensor data is sensitive, based on at least, metadata of the sensor data. For example, the metadata of the sensor data may include an identifier that indicates whether the sensor data is sensitive. Sensitive data may include data that was received during a privacy mode. Advantageously, the processor may be able to quickly determine whether the sensor data is sensitive based on the metadata which may lead to faster processing times and/or improved efficiency. In some implementations, the processor may additionally or alternatively, at block 953, determine whether the sensor data is not sensitive. In some implementations, sensor data that is either sensitive or not sensitive. In some implementations, sensor data cannot be both sensitive and not sensitive.

If the processor determines that the sensor data is sensitive, the processor may proceed to block 955. If the processor determines that the sensor data is not sensitive, the processor may proceed to block 957.

At block 955, the processor may prevent the sensor data from being communicated to other computing devices. For example, the processor may cause a communication device of a mobile device to not communicate the sensor data.

At block 956, the processor may prevent a third-party application from accessing or obtaining the sensor data. The third-party application may be an application executed by the processor on the mobile device. The third-party application may be downloaded from a remote server. The third-party application may be a mobile app. In some implementations, the processor may prevent the third-party application from accessing the sensor data regardless of any permission granted to the third-party application by the user to access data, such as user authorizations during initial download. In some implementations, the processor may prevent access to the sensor data to all third-party applications currently on the mobile device and/or to all third-party applications that may be downloaded to the mobile device in the future.

At block 957, the processor may cause or allow the sensor data to be communicated to other computing devices. For example, the processor may cause a communication device of a mobile device to communicate the sensor data. Communicating the sensor data can include transmitting the sensor data (for example, wirelessly) to one or more remote computing devices or servers.

At block 958, the processor may allow a third-party application to access the sensor data. In some implementations, the processor may allow access to the sensor data to all third-party applications currently on the mobile device and/or to all third-party applications that may be downloaded to the mobile device in the future.

Process 950 is provided as an example and is not intended to be limiting of the present disclosure. In some implementations, the processor may communicate and/or not communicate sensor data regardless of whether the sensor data is sensitive.

Figure 10A:
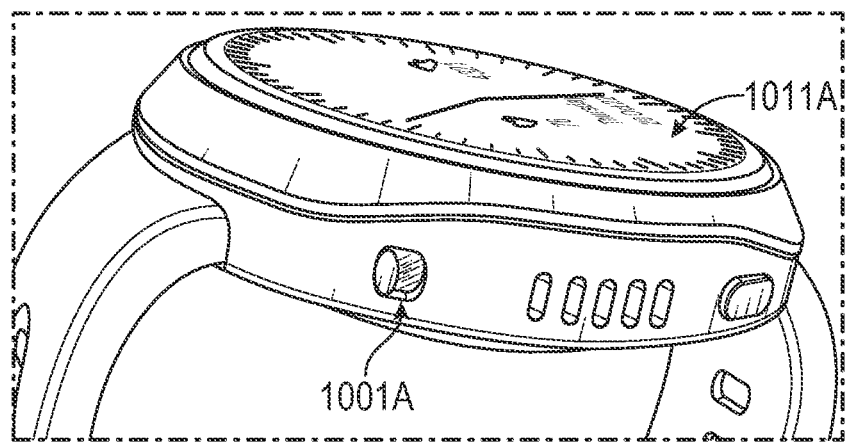
FIG. 10A-10B are perspective views of example implementations of mobile devices.

FIG. 10A is a perspective view of an example implementation of a mobile device 1000A. The mobile device 1000A can include an actuator 1001A and a display 1011A. The display 1011A may be configured to display data, including sensor data obtained by one or more sensors of the mobile device 1011A.

The actuator 1001A may be a slideable switch. The actuator 1001A may be configured to transition between states. For example, the actuator 1001A may slide between a first state and a second state. The actuator 1001A may cause the mobile device 1000A to transition between privacy and non-privacy modes of operation. For example, a user may actuate the actuator 1001A from one state to another to cause the mobile device to enter a privacy mode or a non-privacy mode.

The actuator 1001A, or portion thereof, may include shading or coloring. For example, a portion of the actuator 1001A may be colored red, green, black, or any other color, and may be viewable when the actuator 1001A is in a certain state. In the example implementation shown in FIG. 10A, the actuator 1001A is in a certain state which may cause the mobile device 1000A to enter a privacy mode. A portion of the actuator 1001A may be visible and may be colored a certain color, such as green, black, red, etc., to indicate the mobile device 1000A is in the privacy mode.

In some implementations, the actuator 1001A may be configured to transition between two states which may correspond to a privacy mode and a non-privacy mode. In some implementations, the actuator 1001A may be configured to transition between more than two states. For example, 1001A may be configured to transition between three states which may correspond to a privacy mode, a first privacy mode wherein the sensors are powered on and continue to operate and one or more privacy components, such as a communication device, is powered off and does not operate, and a second privacy mode wherein one or more sensors and one or more privacy components are powered off and do not operate.

During a privacy mode, the display 1011A may be configured to display data such as physiological data obtained from one or more sensors. The display 1011A may be configured to display data that was generated and/or obtained during a privacy mode. Advantageously, a user of the mobile device 1000A may be able to continue to view data via the display 1011A during a privacy mode, while the data is still protected by the mobile device 1011A. In some implementations, the display 1011A may not display data during a privacy mode, for example, because the display 1011A may be powered off during the privacy mode.

Figure 10B:
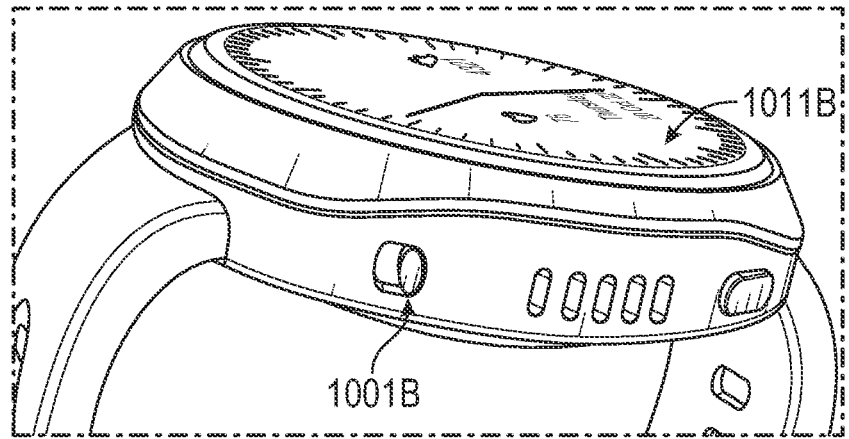

FIG. 10B is a perspective view of an example implementation of a mobile device 1000B. The mobile device 1000B can include an actuator 1001B and a display 1011B. The mobile device 1000A, or its components, such as the actuator 1001B and/or display 1011B may include similar structural and/or operational features as mobile device 1000A shown and/or discussed with respect to FIG. 10A.

The actuator 1001B, or portion thereof, may include shading or coloring. For example, a portion of the actuator 1001B may be colored red, green, black, or any other color, and may be viewable when the actuator 1001B is in a certain state. In the example implementation shown in FIG. 10B, the actuator 1001B is in a certain state which may cause the mobile device 1000B to enter a non-privacy mode. A portion of the actuator 1001B may be visible and may be colored a certain color, such as green, black, red, etc., to indicate the mobile device 1000B is in the non-privacy mode. In some implementations, the portion of the actuator 1001B that is visible in FIG. 10B when the actuator 1001B is in one state may be different than the portion of the actuator 1001A that is visible in FIG. 10A when the actuator 1001A is in another state.

Figure 11:
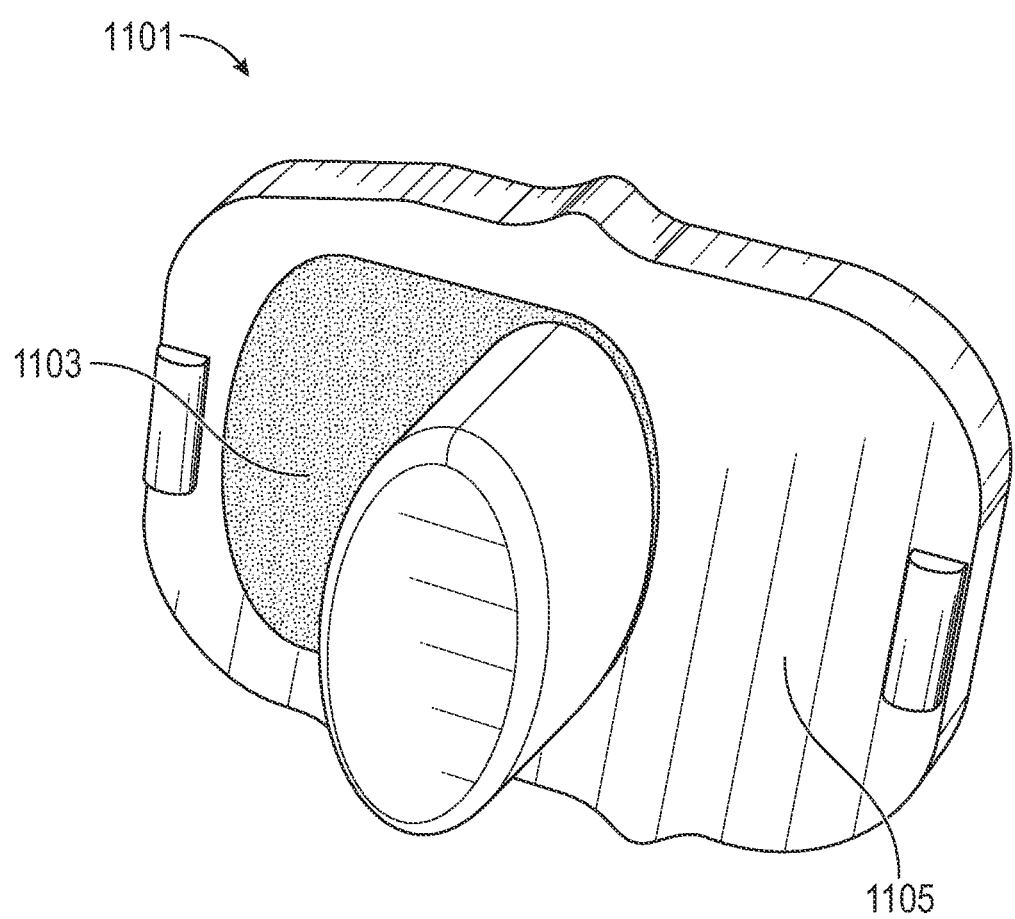
FIG. 11 is a perspective view illustrating an example implementation of an actuator of a mobile device.

FIG. 11 is a perspective view illustrating an example implementation of an actuator 1101. The actuator 1101 may include similar structural and/or operational features as any of the other example actuators shown and/or discussed herein. The actuator 1101 may be implemented in a mobile device such as any of the example mobile devices shown and/or discussed herein. The actuator 1101 may include a first portion 1103 and a second portion 1105. The first portion 1103 may include a first coloring or shading such as red, orange, yellow, green, blue, purple, black, gray, white, brown, or any other color or shade. The second portion may include a second coloring or shading such as red, orange, yellow, green, blue, purple, black, gray, white, brown, or any other color or shade. In some implementations, the first portion 1103 may include a same coloring or shading as the second portion. In some implementations, the first portion 1103 may include a different coloring or shading than the second portion.

The first portion 1103 may be visible when the actuator 1101 is in a certain state and may not be visible when the actuator 1101 is in another state. For example, the first portion 1103 may be exposed to an exterior surface when in one state and not exposed to an exterior surface when in another state. The second portion 1105 may be visible when the actuator 1101 is in a certain state and may not be visible when the actuator 1101 is in another state. The first portion 1103 may not be visible when the second portion 1105 is visible and vice versa.

Figure 12B:
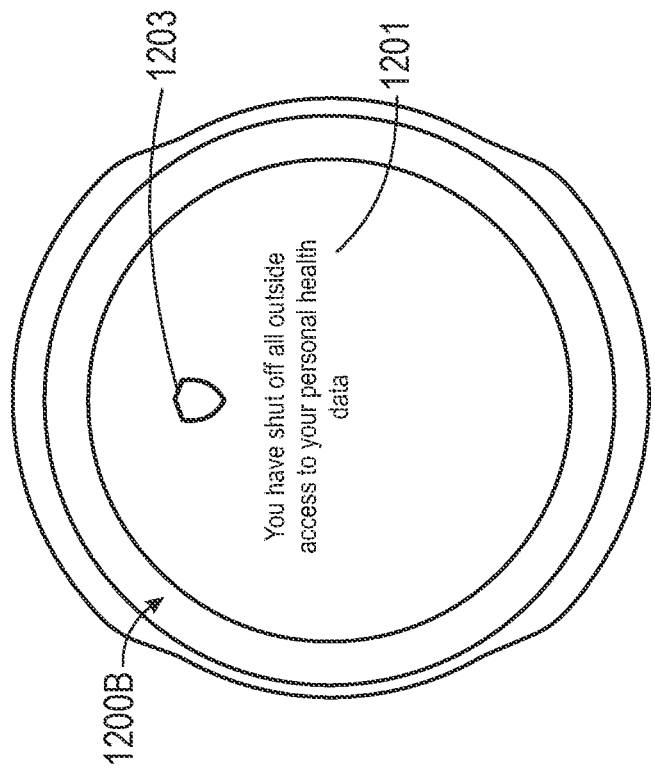
FIGS. 12A-12D illustrate example displays of a mobile device which may display user interfaces.
Figure 12A:
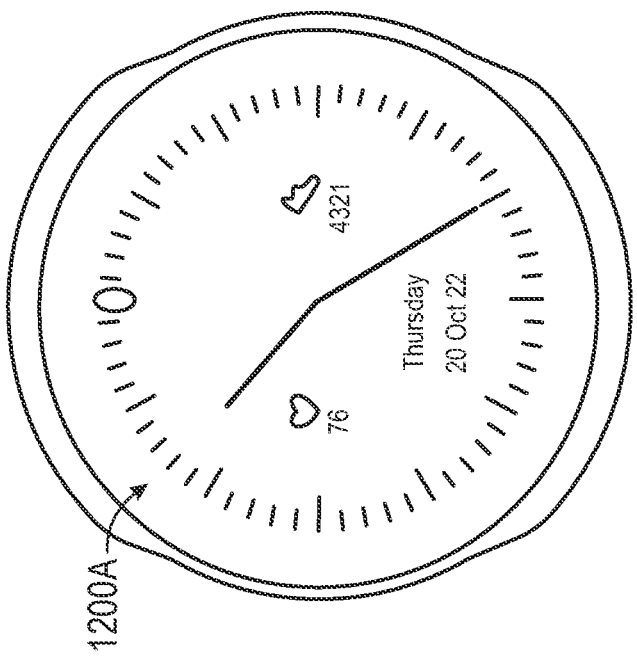

FIGS. 12A-12D illustrate example displays of a mobile device which may display user interfaces. The displays may include digital displays such as LED and/or LCD displays. As shown in FIG. 12A, the display 1200A can display time, such as an analog watch face, date, and sensor data and/or icons, including physiological parameters such as heart rate and step counter. The display 1200A may be displayed during a non-privacy mode.

As shown in FIG. 12B, the display 1200B can display a first indication 1201 that the mobile device has entered a privacy mode. The first indication 1201 can indicate to a user what will happen to certain data during the privacy mode. The display 1200B can display a second indication 1203 to indicate that the mobile device is in a privacy mode.

Figure 12D:
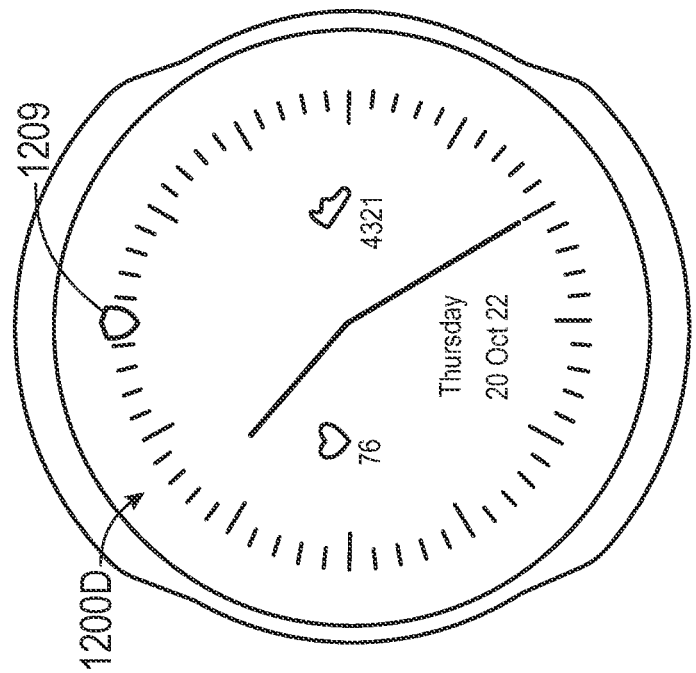
Figure 12C:
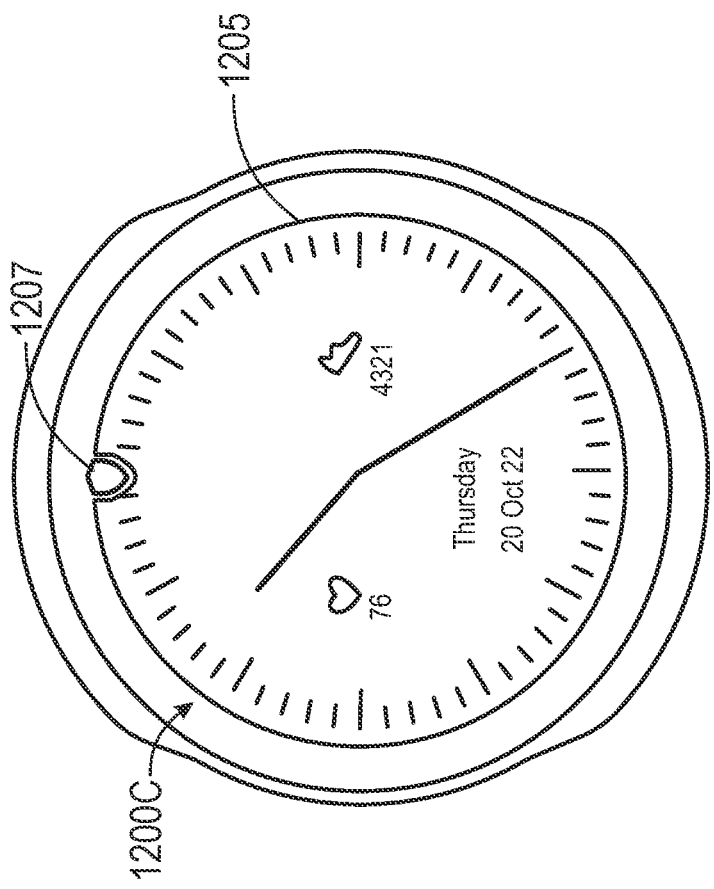

As shown in FIG. 12C, the display 1200C can display time, such as an analog watch face, date, and sensor data, including physiological parameters such as heart rate and step counter). The display 1200C may be displayed during a privacy mode. The display 1200C can display a first indication 1205 that the mobile device is in a privacy mode. The first indication 1205 may be annular or semi-annular. In some implementations, the first indication 1205 may be rectangular. The first indication 1205 may circumscribe the display 1200C. The first indication 1205 may circumscribe a watch face. The display 1200C may display the first indication 1205 upon activation of the privacy mode. For example, the display 1200C may display the first indication 1205, for a length of time after entering privacy mode and may not display the first indication 1205 for an entire duration of the privacy mode. The display 1200C may display a second indication 1207 that the mobile device is in a privacy mode. The display 1200C may display the second indication 1207 for an entire duration of the privacy mode.

As shown in FIG. 12D, the display 1200D can display time, such as an analog watch face, date, sensor data, including physiological parameters such as heart rate and step counter, and an indication 1209 that the mobile device is in a privacy mode. The display 1200D may display the indication 1209 for an entire duration of the privacy mode. The display 1200D may display sensor data during a privacy mode. For example, the display 1200D may display sensor data in real-time as the sensor data is generated by the sensors.

Terminology

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The following description is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

Features, materials, characteristics, or groups described in conjunction with a particular aspect, implementation, or example are to be understood to be applicable to any other aspect, implementation or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing implementation. The protection extends to any novel one, or any novel combination, of the features disclosed in this specification (including any accompanying claims, abstract and drawings), or to any novel one, or any novel combination, of the steps of any method or process so disclosed.

While certain implementations have been described, these implementations have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some implementations, the actual steps taken in the processes illustrated or disclosed may differ from those shown in the figures. Depending on the implementation, certain of the steps described above may be removed, others may be added. For example, the actual steps or order of steps taken in the disclosed processes may differ from those shown in the figures. Depending on the implementation, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific implementations disclosed above may be combined in different ways to form additional implementations, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain implementations, examples and applications, it will be understood by those skilled in the art that the present disclosure extends beyond the specifically disclosed implementations to other alternative implementations or uses and obvious modifications and equivalents thereof, including implementations which do not provide all of the features and advantages set forth herein. Accordingly, the scope of the present disclosure is not intended to be limited by the specific disclosures of preferred implementations herein, and may be defined by claims as presented herein or as presented in the future.

Conditional language, such as "can," "could," "might," or "may," unless specifically stated otherwise, is otherwise understood within the context as used, is generally intended to convey that certain implementations include, while other implementations do not include, certain features, elements, or steps. Thus, such conditional language is not generally intended to imply that features, elements, or steps are in any way required for one or more implementations or that one or more implementations necessarily include logic for deciding, with or without user input or prompting, whether these features, elements, or steps are included or are to be performed in any particular implementation. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain implementations require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred implementations in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A mobile device comprising:
   a power source configured to provide power to one or more components of the mobile device;
   one or more sensors configured to generate sensor data;
   a communication component removably coupled to the power source to receive power therefrom and configured to communicate with one or more computing devices remote to the mobile device;
   an actuator comprising a hardware component configured to physically transition between at least a first state and a second state to cause the communication component to electrically disconnect from the power source when in the second state to terminate communication of the communication component with the one or more computing devices remote to the mobile device, wherein the one or more sensors are electrically coupled to the power source to continue to receive power therefrom to continue to operate to generate the sensor data when the actuator transitions to the second state to electrically disconnect the communication component from the power source; and one or more hardware processors configured to execute program instructions to cause the mobile device to perform one or more application operations when the actuator is in the second state.

2. The mobile device of claim 1, wherein the one or more hardware processors are further configured to execute the program instructions to:

when the actuator is in the first state, cause the communication component to communicate at least a portion of the sensor data based on at least metadata associated with the sensor data, the metadata indicating a sensitivity of the sensor data.

3. The mobile device of claim 1, wherein the sensitivity of the sensor data corresponds to whether the sensor data was generated when the actuator is in the first state or in the second state.

4. The mobile device of claim 1, further comprising:

a data storage device configured to store sensor data generated by the one or more sensors, wherein the data storage device is configured to receive the sensor data when the actuator is in the first state or the second state.

5. The mobile device of claim 1, wherein the one or more hardware processors is further configured to execute the program instructions to:

cause the one or more sensors to perform one or more operations, wherein the hardware processor is configured to communicate with the one or more sensors when the actuator is in the first state or the second state.

6. The mobile device of claim 1, wherein the one or more hardware processors is further configured to execute the program instructions to cause the mobile device to:

access first sensor data generated by the one or more sensors when the actuator is in the first state;

store said first sensor data in a first partition of memory of a storage device of the mobile device;

access second sensor data generated by the one or more sensors when the actuator is in the second state; and store said second sensor data in the first partition of memory of the storage device.

7. The mobile device of claim 1, wherein the actuator is physically separate from the one or more sensors.

8. The mobile device of claim 1, wherein the actuator does not mechanically prevent the one or more sensors from obtaining data.

9. The mobile device of claim 1, wherein transitioning the actuator between the first state and the second state does not prevent the one or more sensors from obtaining data.

10. The mobile device of claim 1, wherein the mobile device is a wearable device.

11. The mobile device of claim 1, wherein the mobile device is a watch.

12. The mobile device of claim 1, wherein transitioning the actuator between the first state and the second state causes the mobile device to transition between a privacy and a non-privacy mode.

13. The mobile device of claim 1, wherein the communication component includes one or more of a transceiver or an antenna.

14. The mobile device of claim 1, wherein the communication component is configured to communicate via one or more wireless communication protocols.

15. The mobile device of claim 1, wherein the communication component is configured to transmit the sensor data to the one or more computing devices.

16. The mobile device of claim 1, wherein the actuator is disposed on a housing of the mobile device.

17. The mobile device of claim 1, wherein the actuator is a switch.

18. A method of toggling a privacy mode of a mobile device, the method comprising:

electrically coupling a communication component of a mobile device to a power source to cause the communication component to establish communication with one or more computing devices remote to the mobile device, wherein the communication component is configured to communicate data with the one or more computing devices when in communication with the one or more computing devices;

physically transitioning an actuator between at least a first state and a second state to cause the communication component to electrically disconnect from the power source when in the second state to terminate communication between the communication component and the one or more computing devices remote to the mobile device;

providing power to one or more sensors from the power source to cause the one or more sensors to generate sensor data when the actuator transitions to the second state to electrically disconnect the communication component from the power source; and causing the mobile device to perform one or more application operations when the actuator is in the second state.

19. The method of claim 18, further comprising:

accessing first sensor data generated by the one or more sensors when the actuator is in the first state;

storing said first sensor data in a first partition of memory of a storage device of the mobile device;

accessing second sensor data generated by the one or more sensors when the actuator is in the second state; and storing said second sensor data in the first partition of memory of the storage device.

20. A non-transitory computer-readable media including computer-executable instructions that, when executed by a computing system, cause the computing system to perform operations comprising:

electrically coupling a communication component of a mobile device to a power source to cause the communication component to establish communication with one or more computing devices remote to the mobile device, wherein the communication component is configured to communicate data with the one or more computing devices when in communication with the one or more computing devices;

physically transitioning an actuator between at least a first state and a second state to cause the communication component to electrically disconnect from the power source when in the second state to terminate communication between the communication component and the one or more computing devices remote to the mobile device;

providing power to one or more sensors from the power source to cause the one or more sensors to generate sensor data when the actuator transitions to the second state to electrically disconnect the communication component from the power source; and causing the mobile device to perform one or more application operations when the actuator is in the second state.

21. The non-transitory computer-readable media of claim 20, wherein the computer-executable instructions, when executed by the computing system, further cause the computing system to perform operations comprising:

when the actuator is in the first state, causing the communication component to communicate at least a portion of the sensor data based on at least metadata associated with the sensor data, the metadata indicating a sensitivity of the sensor data.

* * * * *